(12) United States Patent
Rathore et al.

(10) Patent No.: US 7,626,081 B2
(45) Date of Patent: Dec. 1, 2009

(54) COTTON α-GLOBULIN PROMOTER FOR SEED-SPECIFIC EXPRESSION OF TRANSGENES

(75) Inventors: Keerti S. Rathore, College Station, TX (US); Ganesan Sunilkumar, College Station, TX (US); James P. Connell, Indianapolis, IN (US); Avutu S. Reddy, Carmel, IN (US)

(73) Assignee: The Texas A&M University System, College Station, TX (US)

( * ) Notice: Subject to any disclaimer, the term of this patent is extended or adjusted under 35 U.S.C. 154(b) by 520 days.

(21) Appl. No.: 10/316,786

(22) Filed: Dec. 11, 2002

(65) Prior Publication Data

US 2003/0154516 A1    Aug. 14, 2003

Related U.S. Application Data

(60) Provisional application No. 60/341,266, filed on Dec. 13, 2001.

(51) Int. Cl.
*C12N 15/82* (2006.01)
*C12N 15/84* (2006.01)
*C12N 15/87* (2006.01)
*C12N 15/90* (2006.01)

(52) U.S. Cl. .................. 800/287; 435/468; 800/281; 800/286

(58) Field of Classification Search .................. None
See application file for complete search history.

(56) References Cited

FOREIGN PATENT DOCUMENTS

WO    WO91/13993 A1    9/1991

OTHER PUBLICATIONS

Kim et al. (Plant Molecular Biology, 24:105-117, 1994).*
Chian et al. (Plant Molecular Biology, 9:533-546, 1987).*
Ganesan et al. (Annual Meeting of the American Society of Plant Biologists, p. 7, Jul. 15-19, 2000, San Diego, CA, USA).*
Kinney et al. (Nature Biotechnology, 14:946, 1996). ,.*
Hamada et al. (Transgenic Research, 5:115-121, 1996).*
Quaedvlieg et al. (Plant Molecular Biology, 37:715-727, 1998).*
An G, Ebert PR. Mitra A and Ha SB (1988) Binary vectors. In: Gelvin SB and Shilperoort RA (eds.) Plant Mol Biol Manual (pp. A3: 1-19) Kluwer Academic Publishers, Dordrecht.
Barker S J. Harada JJ and Godberg RB (1988) Cellular localization of soybean storage protein mRNA in transformed tobacco seeds. *Proc Natl Acad Sci USA* 85: 458-462.
Bechtold N and Pelletier G (1998) In planta Agrobacterium-mediated transformation of adult *Arabidopsis thaliana* plants by vacuum infiltration. *Methods Mol Biol* 82:259-266.
Bogue MA. Vonder Haar RA. Nuccio ML. Griffing LR and Thomas TL (1990) Developmentally regulated expression of a sunflower 11S seed protein gene in transgenic tobacco. *Mol Gen Genet* 222: 49-57.
Borroto K and Dure III L (1987) The globulin seed storage proteins of flowering plants are derived from two ancestral genes. *Plant Mol Biol* 8: 113-131.
Bradford MM (1976) A rapid and sensitive method for the quantitation of microgram quantities of protein utilizing the principle of protein-dye binding. *Anal Biochem* 72: 248-254.
Brusslan JA and Tobin EM (1995) Isolation of new promoter-mediated co-suppressed lines in *Arabidopsis thaliana*. *Plant Mol Biol* 27: 809-813.
Bustos MM, Begum D. Kalkan FA. Battraw MJ and Hall TC (1991) Positive and negative *cis*-acting DNA domains are required for spatial and temporal regulation of gene expression by a seed storage protein promoter. *EMBO J* 10: 1469-1479.
Bustos MM, Guiltinan MJ, Jordano J. Begum D, Kalkan FA and Hall TC (1989) Regulation of β-glucuronidase expression in transgenic tobacco plants by an A T-rich, *cis*-acting sequence found upstream of a French bean β-phaseolin gene *Plant Cell* 1:839-853.
Bustos MM, Iyer M and Gagliardi SJ (1998) Induction of a β-phaseolin promoter by exogenous abscisic acid in tobacco: developmental regulation and modulation by external sucros and $Ca^{2+}$ ions. *Plant mol Biol* 37: 265-274.
Cahoon EB, Marillia E-F, Stecca KL, Hall SE, Taylor DC and Kinney AJ (2000) Production of fatty acid components of meadowfoam oil in somatic soybean embryos. *Plant Physiol* 124: 243-251.
Chen Z.-L. Pan N-S and Beachy RN (1988) A DNA sequence element that confers seed-specific enhancement to a constitutive promoter. *EMBO J* 7: 297-302.
Chlan CA, Borrolo K. Kamalay JA and Dure III L (1987) Developmental biochemistry of cottonseed embryogenesis and germination. XIX. Sequences and genomic organization of the α globulin (vicilin) genes of cottonseed. *Plant Mol Biol* 9: 533-546.
Dickinson CD, Evans RP and Nielsen NC (1988) RY repeats are conserved in the 5'-flanking regions of legume seed-protein genes *Nucleic Acids Res* 16: 371.
Dure III L (1989) Characteristics of the storage proteins of cotton. *J Am Oil Chem Soc* 66: 356-359.
Dure III L and Chlan C (1981) Developmental biochemistry of cottonseed embryogenesis and germination. XII. Purification and properties of principal storage proteins. *Plant Physiol* 68: 180-186.

(Continued)

*Primary Examiner*—Vinod Kumar
(74) *Attorney, Agent, or Firm*—Conley Rose P.C.

(57) ABSTRACT

The present invention is directed to 5' regulatory regions of a cotton seed-specific gene, α-globulin. The 5' regulatory region, or parts thereof, when operably linked to either the coding sequence of a native gene, heterologous gene or a sequence complementary to a native plant gene, direct expression of the coding sequence or complementary sequence in a plant seed. The regulatory regions are useful in expression cassettes and expression vectors for the transformation of plants. Also provided are methods of modulating the levels of a native or heterologous gene such as a fatty acid synthesis or lipid metabolism gene by transforming a plant with the subject expression cassettes and expression vectors.

12 Claims, 11 Drawing Sheets
(1 of 11 Drawing Sheet(s) Filed in Color)

OTHER PUBLICATIONS

Forde BG, Hayworth A, Pywell J and Kreis M (1985) Nucleotide sequencing of a B1 hordein gene and the identification of possible upstream regulatory elements in endosperm storage protein genes from barley, wheat and maize. *Nucleic Acids Research* 13: 7327-7339.

Goldberg RB (1986) Regulation of plant gene expression. *Phil Trans R Soc Lond* 314: 343-353.

Goldberg RB, Barker SJ, and Perez-Grau L (1989) Regulation of gene expression during plant embryogenesis. *Cell* 56: 149-160.

Goldberg RB, de Paiva G and Yadegari R (1994) Plant embryogenesis: zygote to seed. *Science* 266: 605-614.

Goossens A, Dillen W, De Clercq J, Van Montagu M and Angenon G (1999) The *arcelin*-5 gene of *Phaseolus vulgaris* directs high seed-specific expression in transgenic *Phaseolus acutifolius* and Arabidopsis plant. *Plant Physiol* 120:1095-1104.

Goto F, Yoshihara T, Shigemoto N, Toki S and Takaiwa F (1999) Iron fortification of rice seed by the soybean ferritin gene. *Nat Biotechnology* 17: 282-286.

Higgins TJV (1984) Synthesis and regulation of major proteins in seeds. *Ann Rev Plant Physiol* 35: 191-221.

Hitz WD, Yadav NS. Reiter RS, Mauvais CJ and Kinney AJ (1995) Reducing polyunsaturation in oils of transgenic canola and soybean. In: Kader J-C and Mazliak (eds.) Plant Lipid Metabolism (pp. 506-508) Kluwer Academic Publishers. Dordrecht.

Horsch RB, Fry JE, Hoffmann N, Neidermeyer J, Rogers SG and Fraley RT (1988) Leaf disc transformation. In: Gelvin SB and Schilperoort RA (eds.) Plant Mol Biol Manual (pp. A5: 1-9) Kulwer Academic Publishers, Dordrecht.

Jefferson RA, Kavanagh TA and Bevan MW (1987) GUS fusions: β-glucuronidase as a sensitive and versatile gene fusion marker in higher plants. *EMBO J* 6: 3901-3907.

Kawagoe Y, Campell BR and Murai N (1994) Synergism between CACGTG (G-box) and CACCTG cis-elements is required for activation of the bean seed storage protein β-*phaseolin* gene. *Plant J* 5: 885-890.

Kawagoe Y and Murai N (1992) Four distinct nuclear proteins recognize *in vitro* the proximal promoter of the bean seed storage protein β-*phaseolin* gene conferring spatial and temporal control. *Plant J* 2: 927-936.

Kim SY, Chung H-J and Thomas TL (1997) Isolation of a novel class of bZIP transcription factors that interact with ABA-responsive and embryo-specification elements in the *Dc3* promoter using a modified yeast one-hybrid system. *Plant J* 11:1237-1251.

Kinney AJ (1996) Development of genetically engineered oilseeds. From molecular biology to agronomics. In: Williams JP. Khan MU, Lem NW (eds.), Physiology, Biochemistry and Molecular Biology of Plant Lipids (pp. 298-300) Kluwer, Dordrecht.

Lessard PA, Allen RD, Fujiwara T and Beachy RN (1993) Upstream regulatory sequences from two β-conglycinin genes. *Plant Mol Biol* 22: 873-885.

Murashige T and Skoog F (1962) A revised medium for rapid growth and bioassays with tobacco tissue cultures. *Physiol Plant* 15: 473-497.

Nunberg AN, Li Z, Bogue MA, Vivekananda J, Reddy AS and Thomas TL (1994) Developmental and hormonal regulation of sunflower helianthinin genes: Proximal promoter sequences confer regionalized seed expression. *Plant Cell* 6: 473-486.

Nunberg AN, Li Z, Chung H-J, Reddy AS and Thomas TL (1995) Proximal promoter sequences of sunflower helianthinin genes confer regionalized seed-specific expression. *J Plant Physiol* 145: 600-605.

Park Y-D, Papp I, Moscone EA, Iglesias VA, Vaucheret H, Matzke AJM and Matzke MA (1996) Gene silencing mediated by promoter homology occurs at the level of transcription and results in meiotically heritable alterations in methylation and gene activity. *Plant J* 9: 183-194.

Russell DA and Fromm ME (1997) Tissue-specific expression in transgenic maize of four endosperm promoters from maize and rice. *Transgenic Res* 6: 157-168.

Seffens WS, Almoguera C, Wilde HD, Haar RAV and Thomas TL (1990) Molecular analysis of a phylogenetically conserved carrot gene: developmental and environmental regulation. *Dev Genet* 11: 65-76.

Shintani D and DellaPenna D (1998) Elevating the vitamin E content of plants through metabolic engineering. *Science* 282: 2098-2100.

Siddiqui NU, Chung H-J, Thomas TL and Drew MC (1998) Abscisic acid-dependent and—independent expression of the carrot late-embryogenesis-abundant-class gene *Dc3* in transgenic tobacco seedlings. *Plant Physiol* 118: 1181-1190.

Siebert PD, Chenchik A, Kellogg DE, Lukyanov KA and Lukyanov SA (1995) An improved PCR method for walking in uncloned genomic DNA. *Nucleic Acids Res* 23: 1087-1088.

Soltis PS, Soltis DE and Chase MW (1999) Angiosperm phylogeny inferred from multiple genes as a tool for comaparative biology. *Nature* 402: 402-404.

Sun SSM and Larkins BA (1993) Transgenic plants for improving seed storage proteins. In: Kung S-d and Wu R (eds.) Transgenic plants: engineering and utilization vol. 1 (pp. 339-372) Academic Press, California.

Sunilkumar G and Rathore KS (2001) Transgenic cotton: factors influencing *Agrobacterium*-mediated transformation and regeneration. *Mol Breeding* 8:37-52.

Sunilkumar G, Vijayachandra K and Veluthambi K (1991) Preincubation of cut tobacco leaf explants promotes *Agrobacterium*-mediated transformation by increasing *vir* gene induction. *Plant Science* 141:51-58.

Vaucheret H (1993) Identification of a general silencer for 19S and 35S promoters in a transgenic tobacco plant: 90 bp of homology in the promoter sequence are sufficient for *trans*-inactivation. *C R Acad Sci. Paris* 316: 1471-1483.

Vivekananda J, Drew MC and Thomas TL (1992) Hormonal and environmental regulation of the carrot *lea*-class gene *Dc3*. *Plant physiol* 100: 576-581.

Ye X, Al-Babili S, Kloti A, Zhang J, Lucca P, Beyer P and Potrykus I (2000) Engineering the provitamin A (β-carotene) biosynthetic pathway into (carotinoid-free) rice endosperm. *Science* 287: 303-305.

Sunilkumar G, Connell JP, Smith CW, Reddy AS and Rathore SR (2002) Cotton alpha-globulin promoter: isolation and functional characterization in transgenic cotton, *Arabidopsis*, and tobacco. *Transgenic Research* 11: 347-359.

PCT International Search Report for PCT/US02/39691.

Ganesan, Sunil K. et al (Poster) "Cotton alpha - Globulin Promoter: a Seed-Specific Promoter for Dicots"; presented at the Annual Meeting of American Society of Plant Biologists, Jul. 15-19, 2000, San Diego, CA.; (p. 7) •.

Ganesan, Sunil K. et al, (Abstract) "Cotton alpha - Globulin Promoter: a Seed-Specific Promoter for Dicots"; Plant Biol. 2000 Program, Poster Sessions, Jul. 2000, p. 194.

Chandler P. And Robertson, M, "Gene Expression Regulated by Abscisic Acid and its Relation to Stress Tolerance," Annu Rev Plant Physiol Plant Mol Biol, 45:113-141 (1994).

Crouch, M. And Sussex, I. "Development and Storage-protein Synthesis in Brassica napus L. embryos in vivo and in vitro," Planta 153:64-74 (1981).

Salinas, J, Oeda, K, and Chua, N-H, "Two G-Box-Related Sequences Confer Different Expression Patterns in Transgenic Tobacco," The Plant Cell 4:1485-1493 (Dec. 1992).

Lam, E and Chua NH, "GT-1 Binding Site Confers Light Responsive Expression in Transgenic Tobacco," Science 248 (4954):471-474 (Apr. 1990).

van der Geest, AHM and Hall, TC, "A 68 bp Element of the β-phaseolin Promoter Functions as a Seed-specific Enhancer," Plant Molecular Biology 32 (4):579-588 (Nov. 1996).

Zakharov, a, Muntz, K, "Seed Legumains are Expressed in Stamens and Vegetative Legumains in Seeds of Nicotiana Tabacum L," J Exp Botany 55(402):1593-1595 (Jul. 2004).

lida, Asako et al. ("Positive and Negative cis-Regulatory Regions in the Soybean Glycinin Promoter Identified by Quantitative Transient Gene Expression," Plant Cell Reports (1995) 14:539-544).

Canevascini, Stefano et al. ("Tissue-Specific Expression and Promoter Analysis of the Tobacco LTP1 Gene," Plant Physiol. (1996) 112: 513-524).

European Patent Office, Office Action dated Nov. 12, 2008, EPO Patent Application No. 02 799 233.8 - 2406, 4 pages.

Indian Patent Office, Examination Report dated May 15, 2007, India Patent Application No. 00855/KOLNP/2004, 6 pages.

Australian Intellectual Property Office, Examination Report dated Jul. 9, 2007, AU Patent Application No. 2002364158, 4 pages.

Australian Intellectual Property Office, Examination Report dated Jan. 2, 2007, AU Patent Application No. 2002364158, 2 pages.

Australian Intellectual Property Office, Examination Report dated Oct. 31, 2005, AU Patent Application No. 2002364158, 2 pages.

Chinese Patent Office, Fourth Office Action dated Feb. 20, 2009, Chinese Patent Application No. 02827579.9, 4 pages.

Chinese Patent Office, Third Office Action dated Jun. 6, 2008, Chinese Patent Application No. 02827579.9, 5 pages.

Chinese Patent Office, Second Office Action dated Jan. 25, 2008, Chinese Patent Application No. 02827579.9, 6 pages.

Chinese Patent Office, First Office Action dated Aug. 3, 2007, Chinese Patent Application No. 02827579.9, 13 pages.

Bray, E. and Beachy, R., Regulation by ABA of "ConglycininExpression in Cultured Developing Soybean Cotyledons," Plant Physiol 79:746-750 (1985).

Delisle, A. and Crouch, M., "Seed storage Protein Transcription and mRNA Levels in Brassica napus during Development and in Response to Exogenous Abscisic acid," Plant Physiol 91:617-623 (1989).

Rivin, C. And Grudt, T., "Abscisic acid and the Developmental Regulation of Embryo Storage Proteins in Maize," Plant Physiol 95:358-365 (1991).

Xu, N. And Bewley, D., "The Role of Abscisic Acid in Germination, Storage Protein Synthesis and Desiccation Tolerance in Alfalfa (*Medicago sativa* L.) seeds," J. Experimental Bot 46(6):687-694 (1995).

Zakharov, a., Giersberg, M., Hosein, F., Meizer, M., Muntz, K., and Saalbach, I., "Seed-Specific Promoters Direct Gene Expression in Non-seed Tissue," J. Exp. Botany 55(402):1463-1471 (Jul. 2004).

Baumlein, H., Boerjan, W., Nagy, I., Bassuner, R., Montagu, M., Inze, D. And Wobus, U., "A Novel Seed Protein Gene from Vicia faba is Developmentally Regulated in Transgenic Tobacco and Arabidopsis Plants," Mol. Gen Genet 225:459-467 (1991).

Nakagawa, H., Ohkura, E. Ohmiya, K. and Hattori, T., "The Seed-Specific Transcription Factor VP1 (OSVP1) is Expressed in Rice Suspension-Cultured Cells," Plant Cell Physiol 37 (3):355-362 (1996).

Thomas, Ms and Flavell, Rb, "Identification of an Enhancer Element for the Endosperm-Specific Expression of High Molecular Weight Glutenin," The Plant Cell. 2:1171-1180 (Dec. 1990).

Marcotte, Jr., Wr, Russell, Sh, and Quatrano Rs, "Abscisic Acid-Responsive Sequences from the Em Gene of Wheat," The Plant Cell 1:969-976 (Oct. 1989).

Burow, M. D., et al.; Developmental control of the β-phaseolin gene requires positive, negative, and temporal seed-specific transcriptional regulatory elements and a negative element for stem and root expression; The Plant Journal; 1992; 537-548; 2(4).

Jefferson, R. A.; Experimental Protocols - Assaying Chimeric Genes in Plants: The GUS Gene Fusion System; Plant Molecular Biology Reporter; 1987; 387-405; 5(1).

Matthews, B. F., et al.; Chapter 11, Reporter Genes and Transient Assays for Plants; Methods in Molecular Biology, Vol. 55: Plant Cell Electroporation and Electrofushion Protocols; J. A. Nickoloff, Ed.; 1995; 147-162; Humana Press Inc., Totowa, New Jersey.

Stomp, A-M.; Chapter 7, Histochemistry Localization of β-Glucuronidase; GUS Protocols: Using the GUS Gene as a Reporter of Gene Expression; 1992; 103-113; Academic Press, Inc.

Van Haaren, M. J. J., et al.; Strong negative and positive regulatory elements contribute to the high-level fruit-specific expression of the tomato 2A11 gene; Plant Molecular Biology; 1991; 615-630; 17; Kluwer Academic Publishers, Belgium.

De Pater, Sylvia, et al., "A 22-bp Fragment of the Pea Lectin Promoter Containing Essential TGAC-like Motifs Confers Seed-Specific Gene Expression," the Plant Cell, 5: 877-886 (1993).

Heppard, Elmer P., et al., "Developmental and Growth Temperature Regulation of Two Different Microsomal ω-6 Desaturase Genes in Soybeans," Plant Physiol, 110: 311-319 (1996).

Van Der Geest, Apolonia H. M., et al., "Cell Ablation Reveals the Expression from the Phaseolin Promoter Is Confined to Embryogenesis and Microsporogenesis," Plant Physiol., 109: 1151-1158 (1995).

Database Biosis 'Online! (2000) Ganesan Sunil K et al: "Cotton alpha-globulin promoter: a seed-specific promoter for dicots." Abstract. *Biosciences Information Service Database* accession no. PREV20030007650.

Sunilkumar G, Connell JP, Smith CW, Reddy AS and Rathore SR (2002) Cotton alpha-globulin promoter: isolation and functional characterization in transgenic cotton, *Arabidopsis*, and tobacco. *Transgenic Research* 11: 347-359.

PCT International Search Report for PCT/US02/39691.

* cited by examiner

```
ctattttcat cctatttaga aatccaagtt gacacctaaa atttagttgg actgccatgt      60
aggattatcg ttagagagat aacggagctt aacggtagag tgatcacttt gtaacaaaat    120
aataacaaaa gtgactaaag tgtaacattt caaacataaa tgattaaaat ataacctgag    180
gcaaacaaaa atgactattt ttatagatta ccctaaaatt aaagagtcat ggccctagcc    240
cctcgcctac ttgtttgttt ttaataaact aacatagtat aatatattgt taggattata    300
taaaattatt aataaatagt ataattaatt taaaat                              336
```

FIG. 10

```
ctattttcat cctatttaga aatccaagtt gacacctaaa atttagttgg actgccatgt      60
aggattatcg ttagagagat aacggagctt aacggtagag tgatcacttt gtaacaaaat    120
aataacaaaa gtgactaaag tgtaacattt caaacataaa tgattaaaat ataacctgag    180
gcaaacaaaa atgactattt ttatagatta ccctaaaatt aaagagtcat ggccctagcc    240
cctcgcctac ttgtttgttt ttaataaact aacatagtat aatatattgt taggattata    300
taaaattatt aataaatagt ataattaatt taaaatttat gaaaaataaa ttaccatatt    360
tcttaaatac gtggcacctt atgttggatt ggactgtata acttatatac tattatctat    420
attgaatcca aatccttact tttaagcgtt tttagtgaaa cattttattt tccattctta    480
ttatataaat ttatataatg atataatatg taatacttag ataatattat tgaaaagaa     540 taaaaatacc tcaaactttg aaaggactaa tttgtatgag catcaaacgt acaggatacc    600
aaaagtatac atatctgaat ttgttcatat ctcctgcaac tcatagatca tcaccatgca    660
cagcaacatg tgtacacttg acttgtcctc tatcaactca accttaact cagtgaatcg     720 ggacatctct gtctcacttt aaaacccttc ccagtttcaa cactctttga attcaactga    780
gttcacatac aacacaacac agtccatcat ctttctgctg ttaaagcatc atcatttcgc    840
cccttccagt tacagatgca acatgaaccc ccctgcaaca aagtttgtcc gaaccttgct    900
agtaccatgt gaagggatgt ggcatctcga tatctaccca ccactataca aaaaaaaaa    960 aaagagacaa tatttcgtct tctttaattt gcacactcgt catcttgcat gtcaatgtct    1020
tcaacacgtt gatgaagatt tgcatgcaaa aatatcacct tccacagctc caccttctat   1080
aaatacatta ccactctttg ctattacc                                       1108
```

FIG. 11

COTTON α-GLOBULIN PROMOTER FOR SEED-SPECIFIC EXPRESSION OF TRANSGENES

RELATED APPLICATION

This application claims the benefit under 35 U.S.C. §119 (e) of U.S. Provisional Patent Application Ser. No. 60/341,266 filed Dec. 13, 2001, entitled "Cotton α-Globulin Promoter For Seed-Specific Expression Of Transgenes," incorporated by reference herein.

FIELD OF THE INVENTION

This invention is in the field of transgene expression. More particularly, the invention is in the field of gene transcription promoter elements useful for transgene expression in plants.

BACKGROUND OF THE INVENTION

Seed-specific transgene expression is required for a number of applications utilizing genetic engineering. These include transgenic means to improve seed nutritional quality by manipulating flux through metabolic pathways (Hitz et al., 1995; Kinney, 1996; Shintani and DellaPenna, 1998; Goto et al., 1999) and for the production of novel compounds of industrial or pharmaceutical value (Cahoon et al., 2000) in a convenient package, the seed. Some of these transgenic traits may require expression of more than one transgene in the developing seed (Ye et al., 2000). In other cases, metabolic engineering to improve seed quality may require over-expression and/or suppression of various genes during seed development. Each step will require a promoter of appropriate strength depending on the desired degree of over-expression or suppression. In addition, a promoter with appropriate developmental timing may also be required. Even if the same degree of expression of more than one gene is required, it is not advisable to use the same promoter for multiple introduced genes. In some cases of high copy number integration of transgenes, promoter homology can lead to gene silencing (Vaucheret, 1993; Brusslan and Tobin, 1995; Park et al., 1996).

Seed storage proteins are expressed at high levels during seed development, and their expression is tightly controlled both spatially and temporally in the developing seed. Therefore, regulatory sequences from genes encoding seed storage proteins represent a valuable source of promoters that can be utilized to drive the expression of transgenes in a seed-specific manner. The promoters from soybean β-conglycinin genes (Barker et al., 1988; Chen et al., 1988; Lessard et al., 1993), French bean phaseolin gene (Bustos et al., 1989, 1991; Kawagoe et al., 1994), sunflower helianthinin gene (Bogue et al., 1990; Nunberg et al., 1995), and the carrot Dc3 promoter (Seffens et al., 1990; Kim et al., 1997) are examples of some of the well-characterized seed-specific promoters from dicots. Despite this array of other promoters available, the problems of expression levels and gene silencing are still an issue. Thus, it is clear that there will be an increasing need for promoters of varying strengths from more than one source to meet the future demands to regulate expression of one or more transgenes in seeds.

SUMMARY OF THE INVENTION

In response to the continuing need for novel promoter elements in the field of plant transgenics, an 1144 bp 5' regulatory legion (SEQ ID NO: 1) comprising an 1108 bp promoter sequence (SEQ ID NO: 2) and a 36 bp 5' transcribed, untranslated sequence from a cotton α-globulin gene was isolated and functionally characterized. Globulins are principal seed storage proteins of cotton and constitute about 60% of total proteins at seed maturity (Dure, 1989). In cotton, two α-globulin genes, gene A and gene B, encode proteins of molecular weight 48 and 51 kDa, respectively (Chlan et al, 1987).

The present invention provides for transgene expression in plants using an α-globulin gene promoter according to the teachings disclosed herein. The α-globulin gene promoter disclosed in this specification addresses the continuing need for novel promoter elements in the field of plant transgenics. In at least one embodiment, the transgene expression is seed specific as defined by the teachings disclosed herein.

In one embodiment, the transgene expression is performed using a promoter DNA containing the 1108 bp α-globulin gene promoter sequence (SEQ ID NO: 2). In a different embodiment, the transgene expression uses a promoter DNA containing an additional sequence that does not interfere with the promoter function of the 1108 bp sequence. In yet another embodiment, the transgene expression uses a promoter DNA containing only part of the 1108 bp sequence such that the promoter function capacity of the partial sequence is functionally similar to the full 1108 bp sequence during seed and plant development.

In one embodiment, an α-globulin gene promoter is used to drive the transcription of an RNA encoding a polypeptide for expression in seed. In a further embodiment, the RNA encodes a polypeptide with commercial value such as an enzyme, an antibody, or peptides for vaccines. In yet another embodiment, an α-globulin gene promoter causes the expression of protein(s) that prevent seed germination. In a further embodiment, an α-globulin gene promoter causes the transcription of an RNA for a polypeptide that improves the nutritional quality of a seed.

In another embodiment, an α-globulin gene promoter drives the transcription of RNAs with desired properties such as an antisense RNA or a ribozyme. In one particular embodiment, the antisense RNA is complementary to the RNA encoding the enzyme involved in the biosynthesis of the toxin, Gossypol expressed in cotton. In another embodiment, the antisense RNA is complementary to RNA for one or more enzymes involved in fatty acid synthesis. In an advantageous embodiment, such RNAs can target viral genomes or transcripts to prevent or reduce disease. In another advantageous embodiment, such RNAs can target and control the expression of endogenous transcripts.

In another embodiment, an α-globulin promoter drives the transcription of a DNA sequence whose transcript will form a hairpin structure that mediates post-transcriptional gene silencing of a native gene through RNA interference. In a different embodiment, an α-globulin gene promoter causes the transcription of an RNA encoding an endogenous protein to silence the gene for that protein through the mechanism of cosuppression (U.S. Pat. No. 6,100,450; Column 12, lines 42–60).

In yet another embodiment, an α-globulin gene promoter drives the expression of transcripts that regulate the fatty acid content of dicot seeds.

BRIEF DESCRIPTION OF THE DRAWINGS

The file of this patent contains at least one photograph executed in color. Copies of this patent with color photographs will be provided by the Patent and Trademark Office upon request and payment of the necessary fee.

A more particular description of the invention, briefly summarized above, may be had by reference to the embodiments thereof which are illustrated in the appended drawings and described herein. It is to be noted, however, that the appended drawings illustrate only some embodiments of the invention and are therefore not to be considered limiting of its scope, because the invention may admit to other equally effective embodiments.

FIG. 10 shows the 336 bp sequence underlined in FIG. 1 and separately set forth in SEQ ID NO:3.

FIG. 11 shows the 1108 bp sequence present in FIG. 1 and separately set forth in SEQ ID NO:2.

DETAILED DESCRIPTION OF A PREFERRED EMBODIMENT

Figure 1:
FIG. 1 shows the α-globulin promoter sequence and reporter gene construct. A Nucleotide sequence of the promoter region (SEQ. ID NO: 1) B T-DNA of the binary vector pBIAGPGUS used in an embodiment of the present invention.

The discussion and examples which follow detail the best known method for performing the invention. It will be recognized that variations of this method may include heterologous or native genes or constructs or modifications to the regulatory sequences, dependent upon the target plant species and the traits to be transferred into the target plants. Cotton, tobacco, and Arabidopsis species were chosen as the target plants in the following examples; however, the use of the cotton α-globulin promoter and method of driving expression of native or heterologous genes outlined below is adaptable to other plants without significant experimentation or deviation from the spirit and scope of this invention.

Globulins are known to be the most prevalent seed storage proteins of dicotyledonous plants (Borroto and Dure, 1987) and their regulatory sequences potentially are a useful source of promoters that can be utilized to confer strong seed-specific expression of transgenes in a wide range of dicot species.

The present invention provides isolated nucleic acids encoding 5' regulatory regions from the seed-specific cotton alpha globulin B (AG) gene, designated as either α-globulin promoter or AGP. In accordance with the present invention, the subject 5' regulatory regions, when operably linked to either a coding sequence of a heterologous gene or a sequence complementary to a native plant gene, direct expression of the coding sequence or complementary sequence in a plant seed. The AG 5' regulatory regions of the present invention are useful in the construction of expression cassettes which comprise in the 5' to 3' direction, a subject AG 5' regulatory region, a heterologous gene or sequence complementary to a native plant gene under control of the regulatory region and a 3' termination sequence. Such an expression cassette can be incorporated into a variety of autonomously replicating vectors in order to construct an expression vector.

Modifications to the AG regulatory regions, including the individual promoters and 5' untranslated regions as set forth in SEQ ID NOS:1 and 2, which maintain the characteristic property of directing seed-specific expression, are within the scope of the present invention. Such modifications include insertions, deletions and substitutions of one or more nucleotides.

Confirmation of seed-specific 5' regulatory regions which direct seed-specific expression and modifications or deletion fragments thereof, can be accomplished by construction of transcriptional and/or translational fusions of specific sequences with the coding sequences of a heterologous gene, transfer of the chimeric gene into an appropriate host, and detection of the expression of the heterologous gene. The assay used to detect expression depends upon the nature of the heterologous sequence. For example, reporter genes, exemplified by chloramphenicol acetyl transferase and β-glucuronidase (GUS), are commonly used to assess transcriptional and translational competence of chimeric constructions. Standard assays are available to sensitively detect the reporter enzyme in a transgenic organism. The β-glucuronidase (GUS) gene is useful as a reporter of promoter activity in transgenic plants because of the high stability of the enzyme in plant cells, the lack of intrinsic β-glucuronidase activity in higher plants and availability of a quantitative fluorimetric assay and a histochemical localization technique. Jefferson et al. (1987b) EMBO J 6; 3901–3907 have established standard procedures for biochemical and histochemical detection of GUS activity in plant tissues. Biochemical assays are performed by mixing plant tissue lysates with 4-methylumbelliferyl-β-D-glucuronide, a fluorimetric substrate for GUS, incubating one hour at 37° C., and then measuring the fluorescence of the resulting 4-methyl-umbelliferone. Histochemical localization for GUS activity is determined by incubating plant tissue samples in 5-bromo-4-chloro-3-indolyl-glucuronide (X-Gluc) for about 18 hours at 37° C. and observing the staining pattern of X-Gluc. The construction of such chimeric genes allows definition of specific regulatory sequences and demonstrates that these sequences can direct expression of heterologous genes in a seed-specific manner.

An aspect of the invention is directed to expression cassettes and expression vectors (also termed herein "chimeric genes") comprising a 5' regulatory region or portion thereof from an AG gene which direct seed specific expression operably linked to the coding sequence of a heterologous gene such that the regulatory element is capable of controlling expression of the product encoded by the heterologous gene. The heterologous gene can be any gene other than AG. If necessary, additional regulatory elements from genes other than AGP or parts of such elements sufficient to cause expression resulting in production of an effective amount of the polypeptide encoded by the heterologous gene are included in the chimeric constructs.

Accordingly, the present invention provides chimeric genes comprising sequences of the AG 5' regulatory region that confer seed-specific expression which are operably linked to a sequence encoding a heterologous gene such as a lipid metabolism enzyme. Examples of lipid metabolism genes useful for practicing the present invention include lipid desaturases such as δ6-desaturases, δ12-desaturases, δ15-desaturases and other related desaturases such as stearoyl-ACP desaturases, acyl carrier proteins (ACPs), thioesterases, acetyl transacylases, acetyl-coA carboxylases, ketoacyl-synthases, malonyl transacylases, and elongases. Such lipid metabolism genes have been isolated and characterized from a number of different bacteria and plant species. Their nucleotide coding sequences as well as methods of isolating such coding sequences are disclosed in the published literature and are widely available to those of skill in the art.

The chimeric genes of the present invention are constructed by ligating a 5' regulatory region or part thereof, of a AG genomic DNA to the coding sequence of a heterologous gene. The juxtaposition of these sequences can be accomplished in a variety of ways. In one embodiment, the order of sequences in a 5' to 3' direction, is an AG promoter, a coding sequence, and a termination sequence. In a preferred embodiment, the order of the sequences in a 5' to 3' direction is an AG promoter, an AG untranslated region, a coding sequence, and a termination sequence which includes a polyadenylation site.

Standard techniques for construction of such chimeric genes are well known to those of ordinary skill in the art and can be found in references such as Sambrook et al. (1989). A variety of strategies are available for ligating fragments of DNA, the choice of which depends on the nature of the termini of the DNA fragments. One of ordinary skill in the art recognizes that in order for the heterologous gene to be expressed, the construction requires at least a promoter and signal for efficient polyadenylation of the transcript. Accordingly, the AG 5' regulatory region that contains the consensus promoter sequence known as the TATA box can be ligated directly to a promoterless heterologous coding sequence.

The restriction or deletion fragments that contain the AG TATA box are ligated in a forward orientation to a promoterless heterologous gene such as the coding sequence of β-glucuronidase (GUS). The skilled artisan will recognize that the subject AG 5' regulatory regions and parts thereof, can be provided by other means, for example chemical or enzymatic synthesis.

The 3' end of a heterologous coding sequence is optionally ligated to a termination sequence comprising a polyadenylation site, exemplified by, but not limited to, the nopaline synthase polyadenylation site, or the octopine T-DNA gene 7 polyadenylation site. Alternatively, the polyadenylation site can be provided by the heterologous gene. Or, 3' UTR which contain RNA localization signal ("zipcode") sequences. These determinants may be important in seed expression systems.

The present invention also provides methods of increasing the expression of a native gene or expressing heterologous genes in plant seeds. In accordance with such methods, the subject expression cassettes and expression vectors are introduced into a plant in order to effect expression of a heterologous gene. For example, a method of producing a plant with increased levels of a product of a fatty acid synthesis or lipid metabolism gene is provided by transforming a plant cell with an expression vector comprising an AG 5' regulatory region or portion thereof, operably linked to a fatty acid synthesis or lipid metabolism gene and regenerating a plant with increased levels of the product of said fatty acid synthesis or lipid metabolism gene.

Another aspect of the present invention provides methods of reducing levels of a product of a gene which is native to a plant which comprises transforming a plant cell with an expression vector comprising a subject AG 5' regulatory region or part thereof, operably linked to a nucleic acid sequence which is complementary to the native plant gene. In this manner, levels of endogenous product of the native plant gene are reduced through the mechanism known as antisense regulation. Thus, for example, levels of a product of a fatty acid synthesis gene or lipid metabolism gene are reduced by transforming a plant with an expression vector comprising a subject AG 5' regulatory region or part thereof, operably linked to a nucleic acid sequence which is complementary to a nucleic acid sequence coding for a native fatty acid synthesis or lipid metabolism gene.

The present invention also provides a method of cosuppressing a gene which is native to a plant which comprises transforming a plant cell with an expression vector comprising a subject 5' AG regulatory region operably linked to a nucleic acid sequence coding for the native plant gene. In this manner, levels of endogenous product of the native plant gene are reduced through the mechanism known as cosuppression. Thus, for example, levels of a product of a fatty acid synthesis gene or lipid metabolism gene are reduced by transforming a plant with an expression vector comprising a subject AG 5' regulatory region or part thereof, operably linked to a nucleic acid sequence coding for a native fatty acid synthesis or lipid metabolism gene native to the plant. Although the exact mechanism of cosuppression is not completely understood, one skilled in the art is familiar with published works reporting the experimental conditions and results associated with cosuppression (Napoli et al. 1990; Van der Krol 1990).

The present invention also provides a method for regulating expression of a native gene which comprises transforming a plant cell with an expression vector comprising a subject 5' AG regulatory region operably linked to a nucleic acid sequence coding for sense part linked to the antisense part of the native plant gene. Transcript from such a construct having self-complementary arms forms a double-stranded RNA, hairpin structure and causes the degradation of transcripts from the native gene leading to post-transcriptional gene silencing (Waterhouse et al., 1998; Wang and Waterhouse, 2000; Chuang and Meyerowitz, 2000). This is similar to RNA-interference mechanisms.

To provide regulated expression of the heterologous or native genes, plants are transformed with the chimeric gene constructions of the invention. Methods of gene transfer are well known in the art. The chimeric genes can be introduced into plants by leaf disk transformation-regeneration procedure as described by Horsch et al. (1988). Other methods of transformation such as protoplast culture can also be used and are within the scope of this invention. In a preferred embodiment, plants are transformed with *Agrobacterium*-derived vectors such as those described in Klee et al. (1987). Other well-known methods are available to insert the chimeric genes of the present invention into plant cells. Such alternative methods include biolistic approaches (described in Klein et al., 1987), electroporation, chemically-induced DNA uptake, and use of viruses or pollen as vectors.

When necessary for the transformation method, the chimeric genes of the present invention can be inserted into a plant transformation vector, e.g. the binary vector described by Bevan (1984). Plant transformation vectors can be derived by modifying the natural gene transfer system of *Agrobacterium tumefaciens*. The natural system comprises large Ti (tumor-inducing)-plasmids containing a large segment, known as T-DNA, which is transferred to transformed plants. Another segment of the Ti plasmid, the vir region, is responsible for T-DNA transfer. The T-DNA region is bordered by terminal repeats. In the modified binary vectors, the tumor inducing genes have been deleted and the functions of the vir region are utilized to transfer foreign DNA bordered by the T-DNA border sequences. The T-region also contains a selectable marker for antibiotic resistance, and a multiple cloning site for inserting sequences for transfer. Such engineered strains are known as "disarmed" *A. tumefaciens* strains, and allow the efficient transfer of sequences bordered by the T-region into the nuclear genome of plants.

Surface-sterilized leaf disks and other susceptible tissues are inoculated with the "disarmed" foreign DNA-containing *A. tumefaciens*, cultured for a number of days, and then transferred to antibiotic-containing medium. Transformed shoots are then selected after rooting in medium containing the appropriate antibiotic, and transferred to soil. Transgenic plants are pollinated and seeds from these plants are collected and grown on antibiotic medium.

Expression of a heterologous or reporter gene in developing seeds, young seedlings and mature plants can be monitored by immunological, histochemical or activity assays. As discussed herein, the choice of an assay for expression of the chimeric gene depends upon the nature of the heterologous coding region. For example, Northern analysis can be used to assess transcription if appropriate nucleotide probes are available. If antibodies to the polypeptide encoded by the heterologous gene are available, Western analysis and immunohistochemical localization can be used to assess the production and localization of the polypeptide. Depending upon the heterologous gene, appropriate biochemical assays can be used. For example, acetyltransferases are detected by measuring acetylation of a standard substrate. The expression of a lipid desaturase gene can be assayed by analysis of fatty acid methyl esters (FAMES).

Another aspect of the present invention provides transgenic plants or progeny of these plants containing the chimeric genes of the invention. Both monocotyledonous and dicotyledonous plants are contemplated. Plant cells are transformed with the chimeric genes by any of the plant transformation methods described above. The transformed plant cell, usually in the form of a callus culture, leaf disk, explant or whole plant (via the vacuum infiltration method of Bechtold et al., 1993) is regenerated into a complete transgenic plant by methods well-known to one of ordinary skill in the art (e.g., Horsh et al., 1985). In a preferred embodiment, the transgenic plant is sunflower, cotton, oil seed rape, maize, tobacco, *Arabidopsis*, peanut or soybean. Since progeny of transformed plants inherit the chimeric genes, seeds or cuttings from transformed plants are used to maintain the transgenic line.

DEFINITIONS

The term "alpha globulin gene promoter and 5' untranslated region" ("AGP") as used herein refers to the 1144 bp DNA sequence shown in FIG. 1A (SEQ ID NO:1), any larger DNA sequence comprising this 1144 bp sequence, and any smaller DNA sequence which is comprised of part of the 1144 bp sequence and which functions transcriptionally in the same manner or in a similar manner as the full length 1144 bp sequence in terms of spatio-developmental expression patterns and/or expression level.

The term "alpha globulin gene promoter" as used herein refers to the non-underlined 1108 bp portion of the DNA sequence shown in FIG. 1A, also separately shown in FIG. 11 and identified as SEQ ID NO:2, any larger DNA sequence comprising this 1108 bp sequence, and any smaller DNA sequence which is comprised of part of the 1108 bp sequence and which functions transcriptionally in the same manner or in a similar manner as the full length 1108 bp sequence in terms of spatio-developmental expression patterns and/or expression level.

As used herein, the term "operatively linked" means that a regulatory region, such as a promoter, is connected to a coding region in such a way that the transcription of that coding region is controlled and regulated by that regulatory region. Methods for operatively linking a promoter to a coding region are well known in the art.

As used herein, the term "cassette" refers to a nucleotide sequence capable of expressing a particular gene if said gene is inserted so as to be operably linked to one or more regulatory regions present in the nucleotide sequence. Thus, for example, the expression cassette may comprise a heterologous coding sequence which is desired to be expressed in a plant seed. The expression cassettes and expression vectors of the present invention are therefore useful for directing seed-specific expression of any number of heterologous genes. The term "seed-specific expression" as used herein, refers to expression in the embryo portion of a plant seed.

EXAMPLES

FIG. 1 shows the α-globulin promoter sequence and reporter gene construct. FIG. 1A (SEQ ID NO:1) shows the isolated and functionally characterized 1144 bp sequence. Putative cis-acting elements are shown inside boxes. The transcription initiation site is indicated with +1. The 5' untranslated region is shown in italics, and the additional unpublished 336 bp sequence that is underlined as shown in FIG. 1A. The 336 bp sequence is shown separately in FIG. 10 and identified as SEQ ID NO:3 Following the method described by Siebert et al. (1995), the 5' flanking promoter region was cloned using the sequence information from an α-globulin clone from a cotton staged-embryo cDNA library. The 772 bp of the clone toward the 3' end of the sequence presented here matched that of the published, 5' genomic flanking sequence for α-globulin gene B (Chlan et al, 1987) Further PCR walks resulted in an additional 336 nucleotides of upstream sequence (shown as underlined sequence in FIG. 1A and separately shown in FIG. 10 and also identified as SEQ ID NO:3). Based on the promoter sequence information, primers were designed to amplify an 1144 nucleotide long fragment containing the combined promoter and the untranslated leader region of the α-globulin B gene from cotton (cv. Coker 312) genomic DNA. The primers used were: AGP5=5'-aag-ctt-gca-tgc-ctg-cag-CTA-TTT-TCA-TCC-TAT-TTA-GAA-ATC-3' (SEQ ID NO: 4); AGP3=5'-ggg-acg-cgt-atc-GAT-TAC-GAT-AAG-CTC-TGT-ATT-TTG-3' (SEQ ID NO: 5) (unique restriction sites incorporated into the primers are indicated in lowercase). The amplified PCR product was cloned into the TA cloning vector; pCRII (invitrogen) resulting in pCRII-AGP. The integrity of the insert was verified by sequencing. Amplification from genomic cotton DNA with the described primers followed by routine cloning and sequencing allows anyone of skill in the art to acquire this DNA fragment without undue experimentation.

The α-globulin promoter from pCRII-AGP was then introduced as a HindIII-XbaI fragment into the polylinker sequence located upstream of the gusA gene in pBI101.3 (Clontech). An out-of-frame ATG (from pCRII polylinker) found upsteam of the GUS coding sequence was removed by deleting the region between the NotI and SmaI sites to create the test construct pBIAGPGUS. The entire putative promoter and 5' UTR were sequenced to verify the integrity of the final construct. The binary vector, pBIAGPGUS, shown in FIG. 1b, which harbors nptII as the plant selectable marker gene, was then introduced into *Agrobacterium* strains LBA4404 and GV3101 using the method described by An et al. (1988).

Referring to FIG. 1A, the TATA box and CAAT box are shown in bold letters and the 5' untranslated region is shown in italics. Visual analysis of the promoter sequence revealed a number of putative DNA motifs that may be involved in tissue-specific transcriptional regulation of the α-globulin gene B. There are four CANNTG motifs (Kawagoe and Murai, 1992), one CATGCACA (RY repeat, Dickinson et al., 1988), and two AACACA motifs (Goldberg, 1986). These cis-elements are believed to confer seed-specific expression to the promoter. Transient expression assays suggest a high degree of tissue (seed)-specificity for the 1108 bp sequence shown in FIG. 11 (SEQ ID NO:2). Functional analyses of this sequence were performed by stable transformation of three different species with a binary vector construct, shown in FIG. 1B, containing the reporter gene, β-glucuronidase, under the control of the α-globulin promoter.

Histochemical localization of GUS activity during seed development. Expression of β-glucuronidase gene, under the control of α-globulin promoter, was first tested using transient expression assays following particle bombardment-mediated transformation of developing embryos, endosperm and leaves of sorghum and cotton. The results (not shown) indicated that the promoter was active only in developing embryos of cotton. On the basis of these results, stable transformations of tobacco, *Arabidopsis*, and cotton were performed for more detailed characterization of the cotton α-globulin promoter activity.

GUS assays were performed on T1 seeds of tobacco and cotton and T2 seeds of *Arabidopsis* as described by Jefferson et al. (1987). These generations of seeds will segregate for transgenes. In order to minimize the variation introduced by null segregants and homozygous seeds, the assay was performed with a large number of seeds. Assays were carried out as triplicates for each transgenic line with 25 (~2 gm), 150 (~15 mg), and 300 (~5 mg) seeds in each replicate for cotton, tobacco and *Arabidopsis*, respectively. Total protein was measured by using the method of Bradford (1976). GUS activity was normalized to the total protein and the results are presented as GUS specific activity (nanomole of 4-MU released per mg protein per min). GUS expression analyses were also carried out in leaf, root, stem and floral tissues of a plant that showed GUS activity in its seeds.

Figure 2:
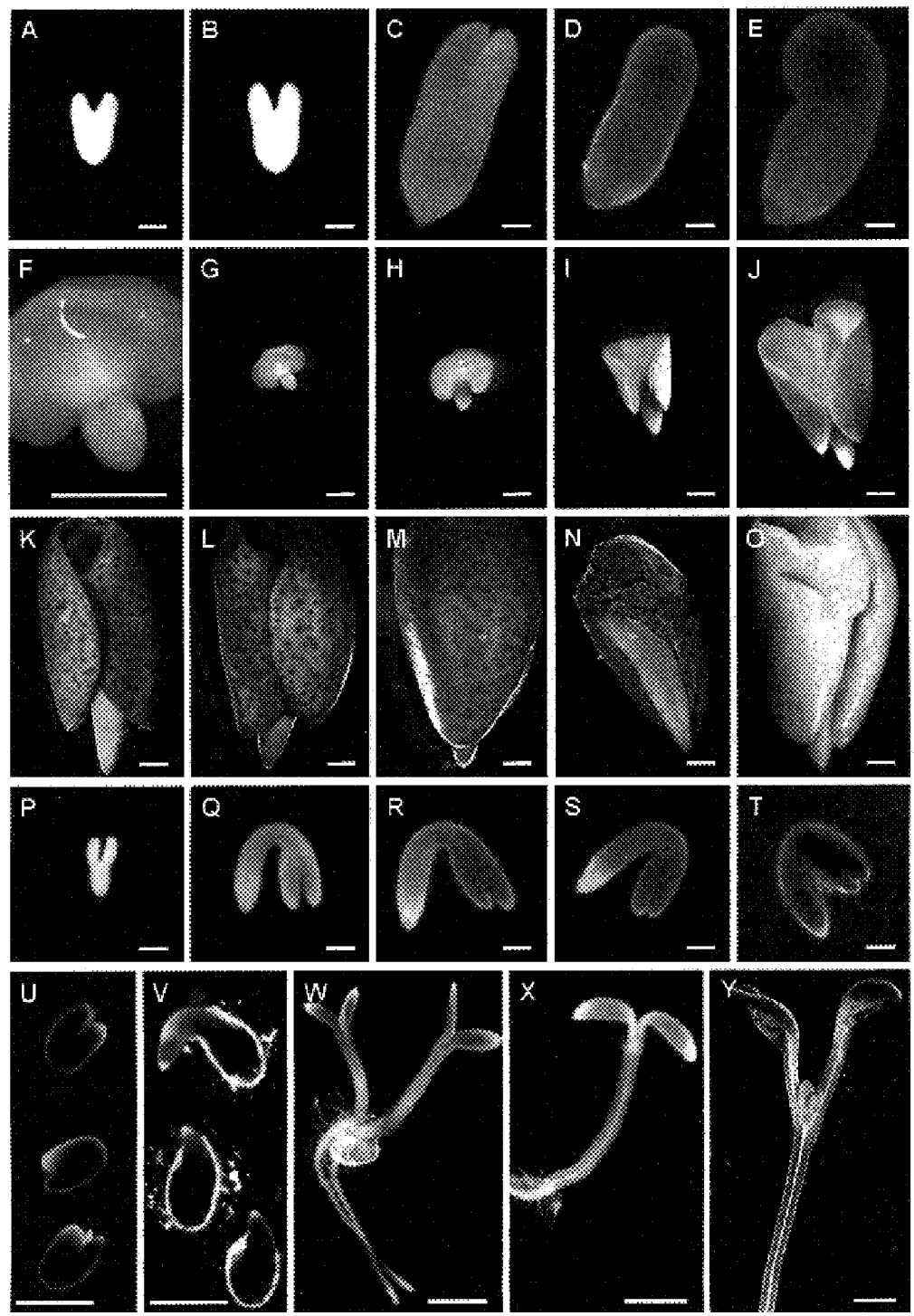
FIG. 2 shows the histochemical localization of GUS activity in developing embryos from stably transformed tobacco, cotton, and Arabidopsis plants and in germinating Arabidopsis seedlings. A–E. Activity in embryos from T1-homozygous tobacco plant: A. embryo 9 days post anthesis (dpa), B. embryo 10 dpa, C. embryo 13 dpa, D. embryo 17 dpa, E. mature embryo from dry seed; F–N. GUS activity in embryos from T1-homozygous cotton plant: F. high magnification image of embryo 16 dpa showing the beginning of GUS activity, G. same embryo at lower magnification, H. embryo 18 dpa, I. embryo 19 dpa, J. embryo 20 dpa, K. embryo 25 dpa, L. embryo 30 dpa, M. embryo 40 dpa, N. embryo isolated from dry seed that has been cut through the middle showing the staining in the radicle and hypocotyl regions; O. embryo from a null segregant cotton seed; P–T: GUS activity in seeds of Arabidopsis thaliana: P. torpedo stage embryo (4 dpa), Q. walking-stick stage embryo (5 dpa), R. upturned-U stage embryo (7 dpa), S. partially mature embryo (9 dpa), T. mature embryo from dry seed; U–Y: GUS activity during seed germination in transgenic Arabidopsis: U. embryos isolated from dry seeds, V. one-day-old seedling, W. 3-day-old seedling, X. 5-day-old seedling, Y. 8-day-old seedling. Bars: A–E, P–T=100 μm; F–O, U–Y=1 mm.

The seeds of T1 homozygous tobacco and T2 homozygous *Arabidopsis* were germinated on MSO medium and the seedlings at different days after germination were histochemically assayed (in the case of *Arabidopsis*) or fluorometrically assayed (in the case of tobacco) for GUS activity. After GUS staining, the seedlings were treated in ethanol to clear chlorophyll. In case of tobacco and *Arabidopsis*, the embryos/seedlings were photographed using Kodak Elitechrome Tungsten 160T film. The slides were then scanned and digitally enlarged. The cotton embryo images were captured using a Zeiss AxioCam digital camera coupled to a Zeiss M²BIO Zoom Stereo/Compound microscope. FIG. 2 was compiled using Canvas 7.0 software.

Seeds from a T0 transgenic cotton plant showing seed-specific GUS expression were first germinated on 100 mg/l kanamycin to eliminate null segregants. Those seeds that germinated and grew in the presence of kanamycin were transferred to soil and grown to maturity. The zygosity status of these T1 plants was determined by GUS histochemical analysis on the seeds. One homozygous plant and one hemizygous plant were selected for quantitative analysis of GUS activity in their seeds. Embryos isolated from the seeds were analyzed individually for GUS activity using the fluorometric procedure described earlier.

FIG. 2 shows the histochemical localization of GUS activity in developing embryos from stably transformed tobacco, cotton, and *Arabidopsis* plants and in germinating *Arabidopsis* seedlings. Histochemical analysis of GUS activity was useful in identifying the timing and localization of α-globulin promoter-regulated expression. Histochemical analysis results for GUS activity in the embryos isolated from seeds at various stages of development in embryos from T1-homozygous tobacco plant are shown in FIGS. 2A–E. AGP:gusA expression was evaluated in the seeds from three T1-homozygous tobacco plants. *Nicotiana tabacum* cv. Havana was transformed with *Agrobacterium* strain LBA4404(pBIAGP-GUS) using the leaf disc transformation method (Horsch et al., 1988). Transformants were selected on regeneration medium (MS salts, 100 mg/l myo-inositol, 0.4 mg/l thiamine HCl, 4 µM BAP, 0.5 µM NAA, 3% sucrose, pH 5.6, solidified with 0.8% Difco-Bacto agar) containing 100 mg/l kanamycin and 500 mg/l carbenicillin. Regenerated shoots were excised and grown on MSO medium (MS salts, B-5 organics, 2% sucrose, pH 5.7, solidified with 0.8% Difco-Bacto agar) containing 100 mg/l kanamycin and 500 mg/l carbenicillin. Plants with good root systems were transferred to soil and grown to maturity in the greenhouse. Isolation of embryos from seeds of several capsules and their microscopic visualization indicated that embryos reached the heart stage around 9 days post anthesis (dpa). No visible GUS activity was detected in embryos at heart or late heart stages. However, GUS activity was observed in embryos at late torpedo and older stages of development.

FIGS. 2F–2N show GUS activity in embryos from T1-homozygous cotton plant. Histochemical analysis of GUS activity was carried out in developing embryos isolated from the seeds of a T1-homozygous cotton plant. The hypocotyl segments of cotton (*Gossypium hirsutum* cv. Coker 312) seedlings were transformed with *Agrobacterium* [LBA4404 (pBIAGPGUS)] by following the method described by Sunilkumar and Rathore (2001). Plants were regenerated from kanamycin-resistant transgenic calli and grown to maturity. GUS staining was first detected in embryos at 16 dpa. At this stage, as shown in FIGS. 2F and 2G, the cotyledons had just begun to expand and GUS activity appeared just below the cotyledons, at the junction of cotyledons and hypocotyl. The activity increased and spread throughout the embryo as the seed development progressed as shown in FIGS. 2H–2N. Intense staining was observed in embryos 40 dpa and in mature embryos isolated from dry seeds. FIG. 2O shows an embryo isolated from a null segregant seed that was negative following histochemical GUS assay. Results from histochemical localization of GUS activity in mature embryos from transgenic plants of three plant species suggests that the 1108 bp promoter region has the required cis-acting domains that confer expression in the embryo.

FIGS. 2P–2T show GUS activity in developing embryos from the seeds of T2-homozygous *Arabidopsis thaliana* C24 plant. Seeds from a homozygous T2 generation of *Arabidopsis* transformed with AGP:gusA were used for histochemical analyses. *Arabidopsis thaliana* C24 plants were transformed by the vacuum infiltration method (Bechtold and Pelletier, 1998) using the *Agrobacterium* strain GV3101 (pBIAGP-GUS). Transformed seeds (T1) were selected on MSO medium containing 50 mg/l kanamycin. The kanamycin-resistant plants were transferred to soil and grown to maturity in a growth room (23° C., 65% humidity, 14h/10h photoperiod).

Expression of AGP:gusA was monitored in the embryos isolated from seeds at various developmental stages. GUS staining was not visible in heart stage and late heart stage embryos (results not shown). A low level of GUS activity was observed in the torpedo stage embryos, shown in FIG. 2P, and the intensity of blue staining progressively increased as the embryos grew to maturity as shown in FIGS. 2Q–2T. An intense GUS staining was found in the embryos isolated from dry seeds. Taken together, results from these three dicot species suggest that gene expression driven by AGP is confined to middle to late stages of embryo development.

FIGS. 2U–2Y show GUS activity during seed germination in transgenic *Arabidopsis*. In order to determine if AGP activity is confined strictly to developing embryos/seeds, GUS activity was monitored in germinating *Arabidopsis* seedlings. GUS activity was analyzed in germinating seedlings using the histochemical method. Results presented in FIGS. 2U–Y show that the intensity of GUS staining decreased progressively as the seedlings grew. At 5 days post imbibition, there was still some residual GUS activity visible. However, after 7 days, faint patches of blue staining were observed only at the two ends of the hypocotyl. GUS staining was not visible in cotyledons, root or in the middle portion of the hypocotyl. No GUS activity was observed in seedlings beyond 7 days post imbibition (FIG. 2Y).

Figure 3:
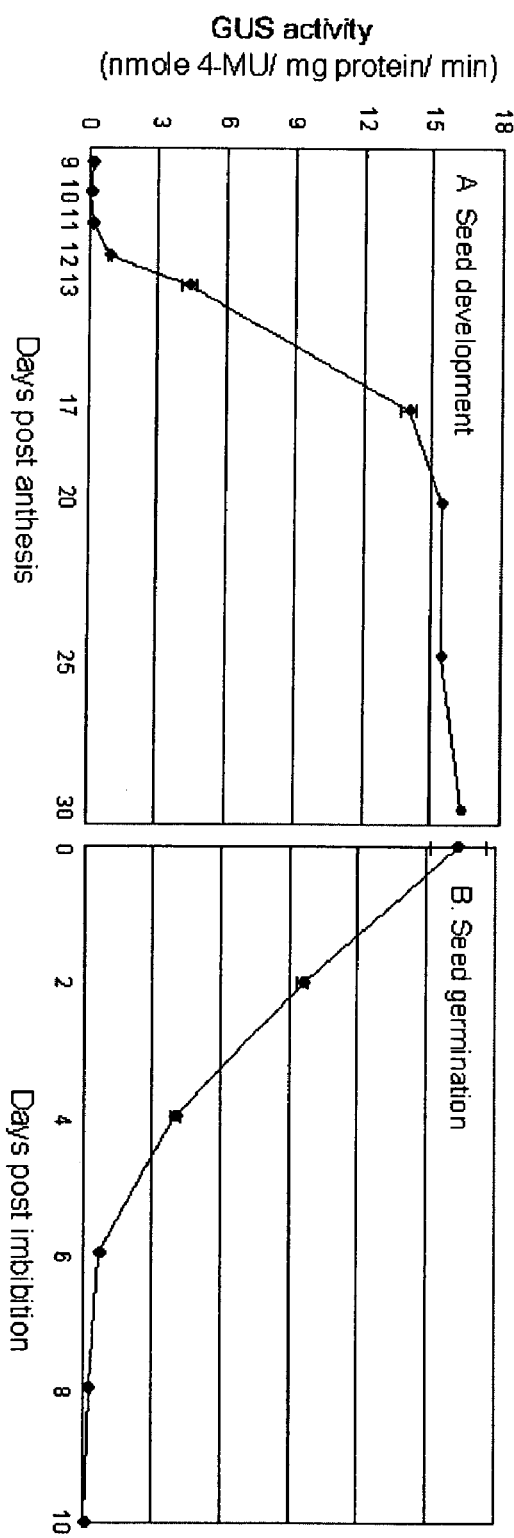
FIG. 3 shows the developmental regulation of GUS expression by the α-globulin promoter in tobacco. A. Developmental regulation of GUS expression by the α-globulin promoter in tobacco seeds. B. GUS specific activity in tobacco seedlings during germination at different days post imbibition.

FIG. 3 shows the developmental regulation of GUS expression by the α-globulin promoter in tobacco via quantitative analysis. Histochemical analysis does not permit detection of low levels of GUS activity and also does not give a precise measure of increase in the level of GUS expression. Therefore, AGP activity during seed development was studied by monitoring GUS expression in developing seeds (tobacco) and developing embryos (cotton) by quantitative, fluorometric GUS assay at various time points after flowering. As shown in FIG. 3A, measurable GUS-specific activity was first detected at 12 dpa in the seeds from a T1 homozygous tobacco plant. The activity then increased rapidly, finally reaching a maximum at 20 dpa.

FIG. 3B shows GUS activity in tobacco seedlings during germination at different days post imbibition. Surface sterilized seeds from a T1 homozygous tobacco plant were germinated on MS medium (Murashige and Skoog, 1962). GUS fluorometric assay was carried out using the extracts from whole seedlings at 0, 2, 4, 6, 8 and 10 days post imbibition. GUS activity decreased continuously following seed germination (FIG. 3B) and only 2% of the initial activity was found after 8 days. No GUS activity was detected in seedlings 10 days after germination. The fact that GUS activity rapidly drops to undetectable levels following seed germination in both *Arabidopsis* (FIGS. 2A–2E) and tobacco (FIG. 3B) suggests that the promoter is active only during seed development and inactive during seed germination and in mature plant.

Figure 4:
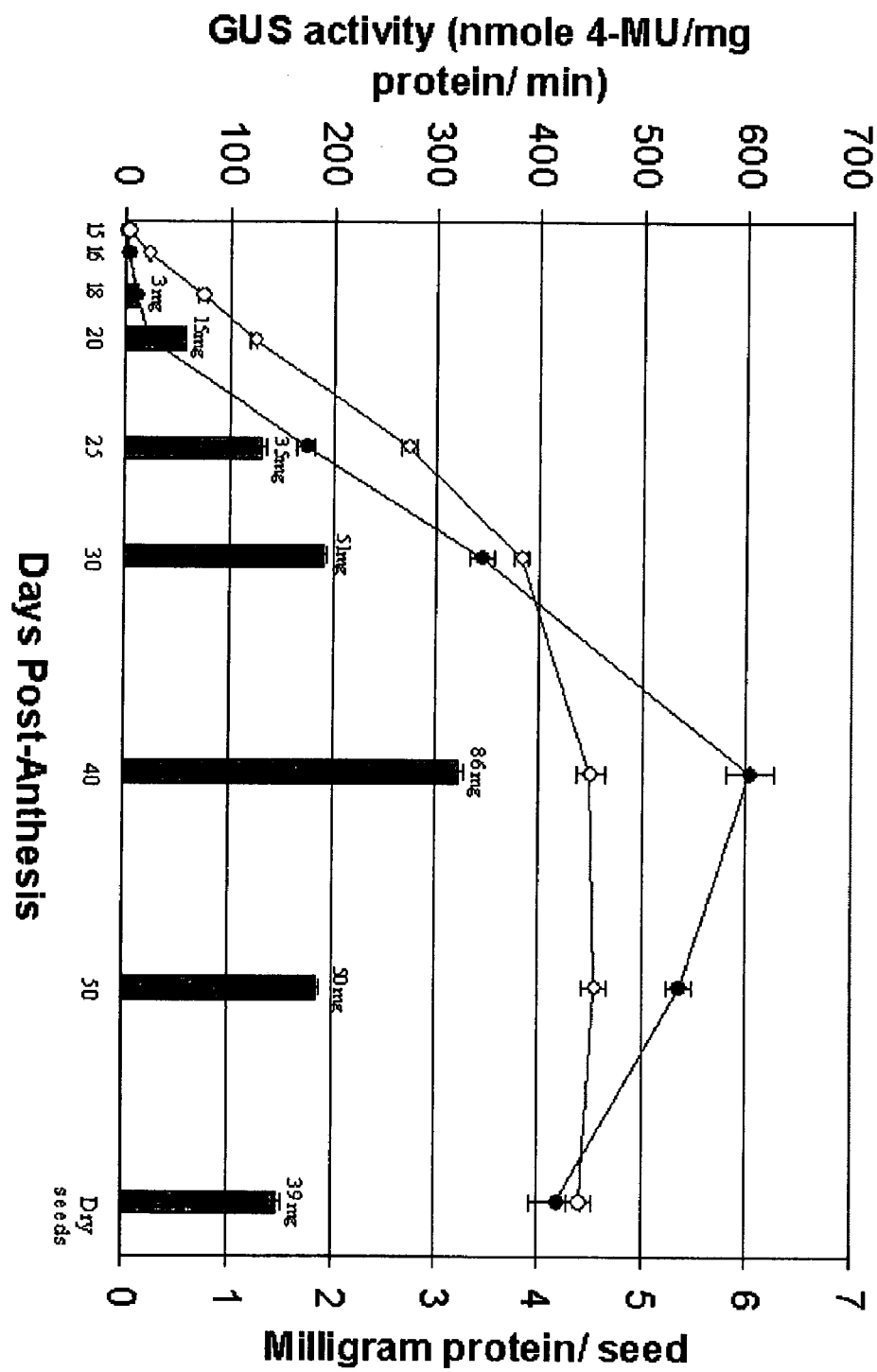
FIG. 4 shows the developmental regulation of GUS expression by the α-globulin promoter in cotton embryos. GUS specific activity (closed circle) and total protein (open circle) in extracts from developing cotton embryos as a function of days post anthesis (dpa).

FIG. 4 shows the developmental regulation of GUS expression by the α-globulin promoter in cotton embryos via quantitative analysis. Because of large seed size, the relatively slow process of embryo development, and the ease with which the embryos can be isolated from developing seeds, cotton offered the best system to carry out detailed characterization of AGP:gusA expression at the single seed level. The results from quantitative analysis for GUS activity, protein levels and fresh weight in developing embryos, isolated from the seeds from a T1 homozygous cotton plant, are shown in FIG. 4. This plant was grown in the greenhouse in the month of April and at this time of the year, the bolls opened at about 43 dpa. GUS expression was first detected at 15 dpa (60 pmoles/mg protein/min). Thereafter, there was a slow increase in GUS activity till 20 dpa, followed by a rapid rise until 40 dpa. From this peak until seed maturity, there was a small but statistically significant decline in activity. During seed development, the protein levels (as measured in the GUS extraction buffer) increased rapidly from 15 dpa to 30 dpa, followed by a slow increase till 40 dpa before leveling off. It was not possible to accurately weigh the embryos before 18 dpa. However, from this point on, embryo fresh weight increased until 40 dpa, followed by a decrease as the seed reached dry state. These results confirm the histochemical analysis. The AGP:gusA expression begins in cotton embryos at around 15 dpa, and the activity either levels off or declines beyond 40 dpa.

Table 1 shows GUS specific activity in various tissues of a T1-homozygous transgenic cotton plant and in control seeds. Histochemical GUS analysis was performed on various parts of three different T0 transgenic cotton plants that expressed the reporter gene in the embryos. GUS activity-dependent histochemical staining was not detected in tissues such as stem, leaf, petiole, flower stock, sepals, petals or square of the transgenic plant. In addition, more sensitive fluorometric analyses were performed to detect AGP activity in different organs and tissues of one of the transgenic cotton plant. Results from this analysis, presented in Table 1, show clearly that no measurable GUS activity was present in stem, leaf, floral bud, pollen, and root. A high level of GUS activity was detected only in the seeds. These results suggest that AGP-driven transgene activity is tightly controlled and is specific to the seed.

TABLE 1

GUS specific activity in various tissues of a T1-homozygous transgenic cotton plant and in control seeds.

| Tissue type | GUS activity[a] (nmole 4-MU/mg protein/min) |
| --- | --- |
| Stem | 0.018 ± 0.002 |
| Leaf | 0.014 ± 0.005 |
| Root | 0.12 ± 0.006 |
| Floral bud | 0.11 ± 0.05 |
| Pollen | 0.024[b] |
| Transgenic seed[c] | 349.9 ± 55 |
| Control seed[c] | 0.002 ± 0.0004 |

[a]Values are mean GUS activity ± SE from three replicates.
[b]The number of replicates were not sufficient to calculate SE (5.7 mg pollen was used in the assay).
[c]Assay was performed in embryos collected from 10 seeds for each replicate.

Figure 5:
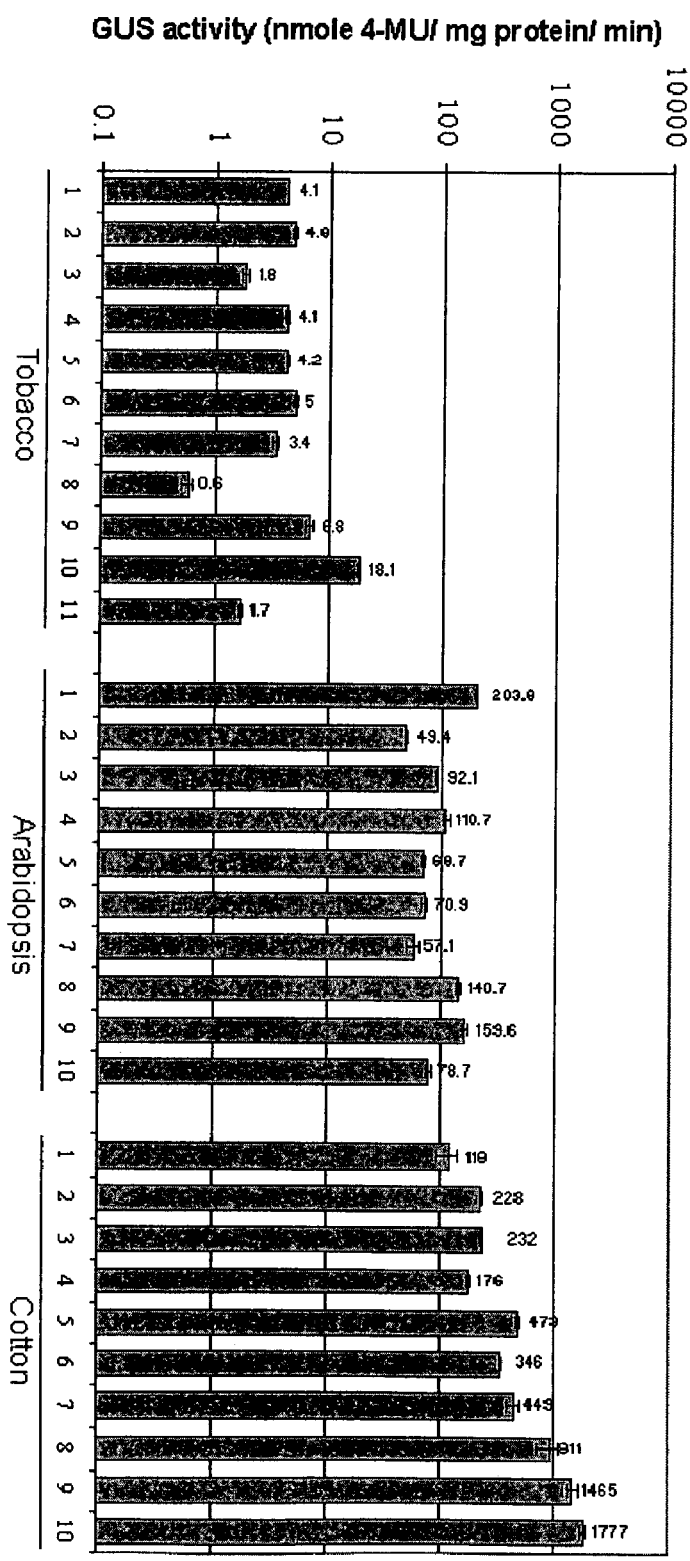
FIG. 5 shows GUS activity in seeds from independent transgenic lines of T0 tobacco, T1 Arabidopsis, and T0 cotton.

FIG. 5 shows GUS activity, plotted on a log scale, in seeds from independent transgenic lines of T0 tobacco, T1 *Arabidopsis*, and T0 cotton. Preliminary results had indicated that AGP-driven GUS activity differed greatly amongst these three species. Extensive analyses were performed on seeds from a number of independent transgenic lines (that were positive for GUS activity as tested by histochemical method) from *Arabidopsis*, tobacco and cotton to confirm this observation. As shown in FIG. 5, GUS activity in the seeds from 11 independent transgenic tobacco lines ranged from 0.6 to 18 nanomole 4-MU/mg protein/min. Similar analysis in seeds from 10 independent transgenic *Arabidopsis* lines showed a range of 49 to 203 nanomole 4-MU/mg protein/min. GUS activity in 10 independent transgenic cotton lines ranged from 118 to 1777 nanomole 4-MU/mg protein/min. Similar high levels of seed-specific promoter expression has been reported also in maize seeds obtained from glutelin promoter:gusA and zein promoter:gusA transformants (Russell and Fromm, 1997). The results suggest that the cotton AGP, although recognized in different heterologous systems as a seed-specific promoter, showed the highest level of activity in cotton.

Figure 6:
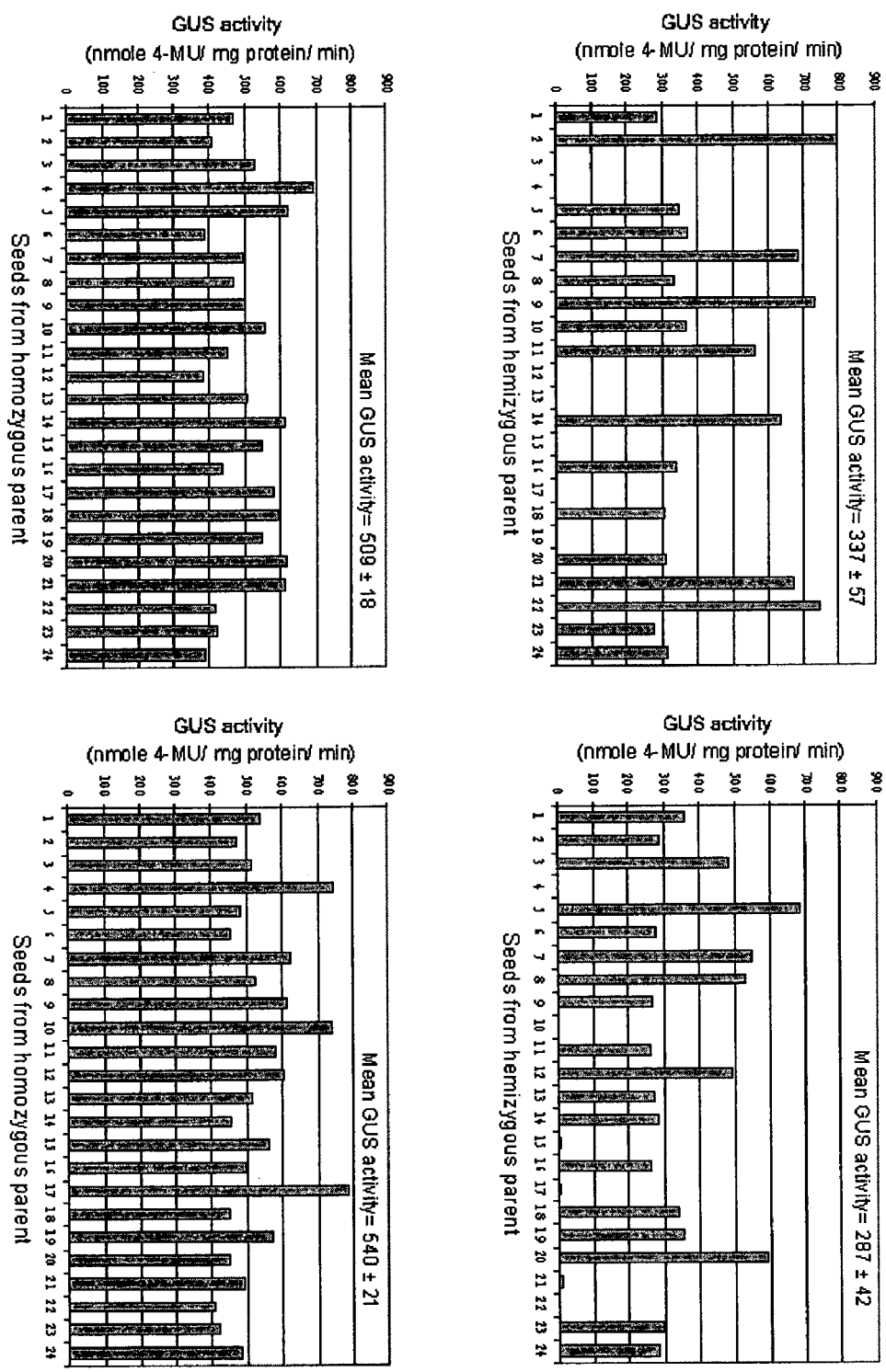
FIG. 6 shows GUS specific activity in individual embryos isolated from seeds from a T1 homozygous and seeds from a single T1 hemizygous cotton plant.

FIG. 6 shows GUS specific activity in individual embryos isolated from seeds from a T1 homozygous and seeds from a single T1 hemizygous cotton plant. Both homozygous and hemizygous T1 pants were derived from a single T0 transgenic line. The large seed size of cotton allowed analysis of GUS activity at a single seed level. This provided us with an opportunity to get a quantitative measure of GUS activity in individual seeds within the segregating T2 seed population produced by a hemizygous T1 plant and compare these values with activities in individual seeds produced by a homozygous T1 plant. As shown in FIG. 6, all of the T2 seeds from the homozygous T1 parent showed GUS activity (FIG. 6, bottom histograms) suggesting that reintroduction of a native promoter, even under homozygous condition, did not result in transgene silencing in this line. T2 seeds from the hemizygous T1 parent showed clear phenotypic segregation (3:1) for the transgene activity (FIG. 6, top histograms). Moreover, among the seeds showing GUS activity, two different levels of activity was apparent in majority of the cases. The higher level activity in about one fourth of T2 seeds from the hemizygous parent was similar to the level seen in the T2 seeds from the homozygous parent. Thus, the two different levels of GUS activity in the seeds from the hemizygous plant may be a result of either hemizygous or homozygous transgenic status of the individual seed suggesting a gene dose effect.

Figure 7:
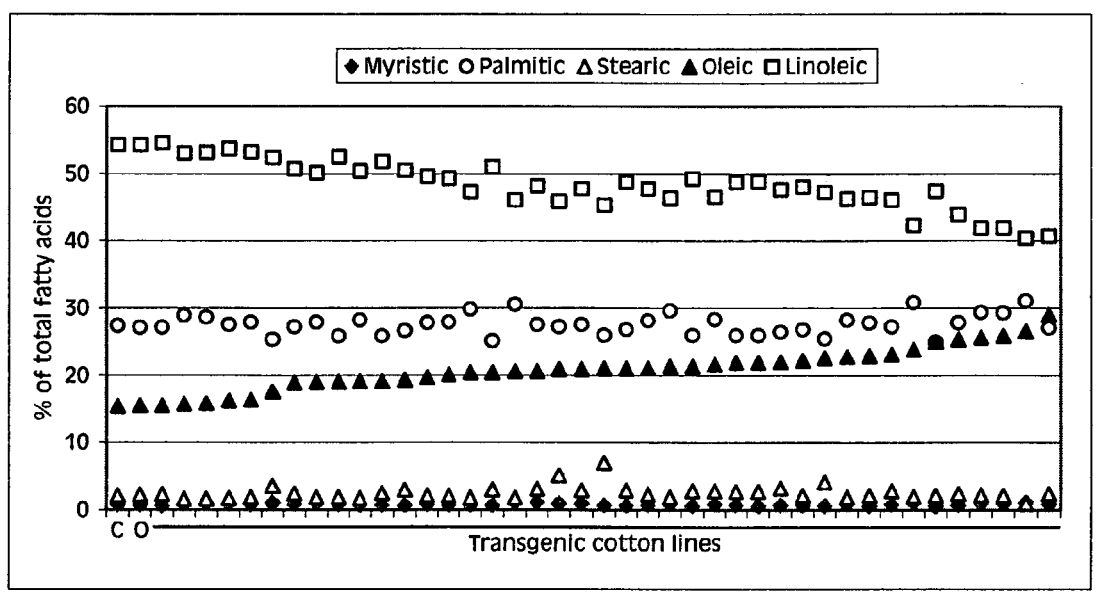
FIG. 7 shows that the α-globulin promoter drives antisense expression of the δ-12 desaturase gene from cotton to increase the levels of oleic acid in different transgenic lines of cottonseeds. C: non-transformed control plant. O: Cottonseed oil (Supelco, Bellefonte, USA).

FIG. 7 shows that the α-globulin promoter drives antisense expression of the δ-12 desaturase gene from cotton to increase the levels of oleic acid in different transgenic lines of cottonseeds. Cotton (Coker 312) was transformed with a construct where a δ-12 desaturase gene from *Gossypium hirsutum*, in antisense orientation was under the control of cotton α-globulin promoter. Cotton transformation was performed as described by Sunilkumar and Rathore (2001). A total of 45 plants were regenerated from 26 independent transgenic callus lines. The kernels from single T1 cotton seeds or a pooled sample of randomly-picked 30 seeds from each plant were homogenized to a fine powder using agate mortar and pestle. Total fatty acids was extracted from a sample of 50 mg of this powder as described by Dahmer et al. (1989). Fatty acid analysis was performed using a gas chromatograph. The results are expressed as percentage of total fatty acids. The fatty acid composition of cottonseed oil is: myristic acid (0.9%), palmitic acid (24.7%), stearic acid (2.3%), oleic acid (17.6%), and linoleic acid (53.3%) (White et al., 2000). The levels of oleic acid in the T1 seeds from transgenic plants ranged from 15% to 29% (FIG. 7). Linoleic acid levels ranged between 53% to 40% in these plants. The lines with decreased levels of linoleic acid showed a concomitant increase in oleic acid levels. This negative correlation is to be expected if the alteration is a result of suppression of δ-12 desaturase activity.

Figure 8:
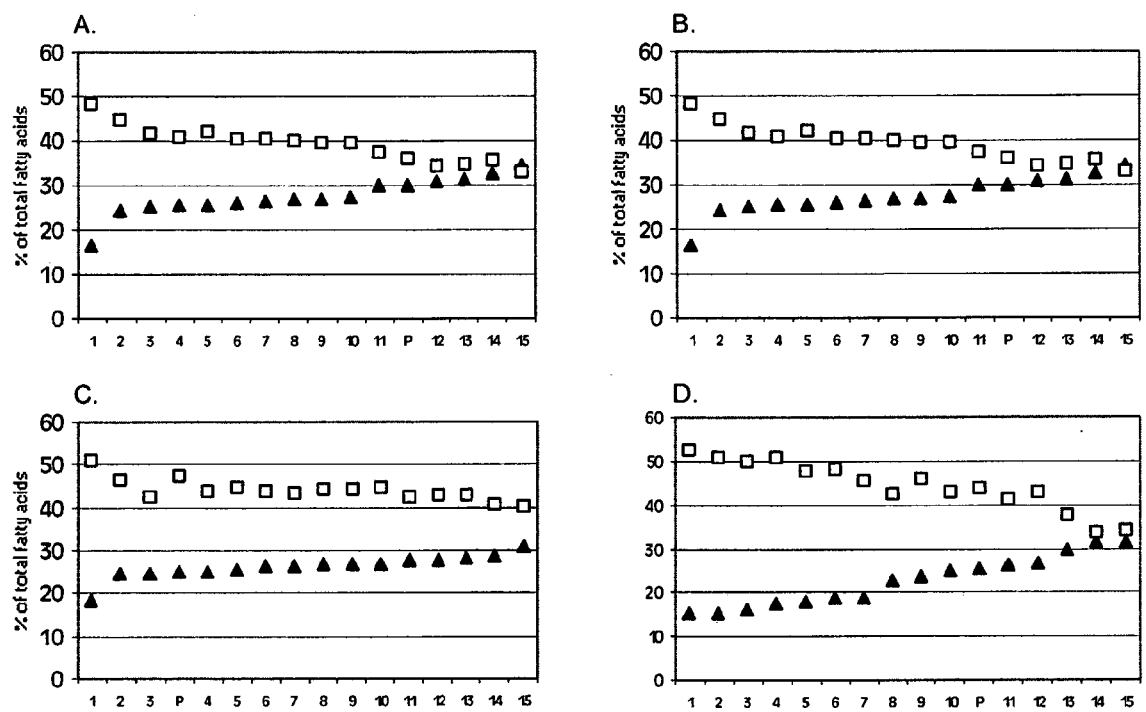
FIG. 8 shows the fatty acid levels of four lines of high-oleate cotton seeds at the individual seed level. Oleic acid (triangle) and linoleic acid (open square) levels in individual T1 seeds from four T0 lines H50-2 (A), H41-1 (B), H4-2 (C) and H42-2 (D). Numbers in the X axis represent individual seeds. P: 30 pooled seeds.

FIG. 8 shows the fatty acid levels of four lines of high-oleate cotton seeds at the individual seed level. Four high-oleate lines were chosen for fatty acid analysis at individual seed level. Since T1 seeds will be segregating for the transgene, a few seeds (null segregants) are expected to have wild type levels of oleic acid/linoleic acid. However, majority of the seeds will exhibit higher oleic acid/lower linoleic acid phenotype. As shown in FIG. 8, some seeds from the transgenic lines H50-2 and H41-1 had oleic acid levels as high as 34.2% and 34.3%, respectively. As expected, few seeds (probably null segregants) from all the four lines exhibited wild-type levels of oleic acid/linoleic acid.

Figure 9:
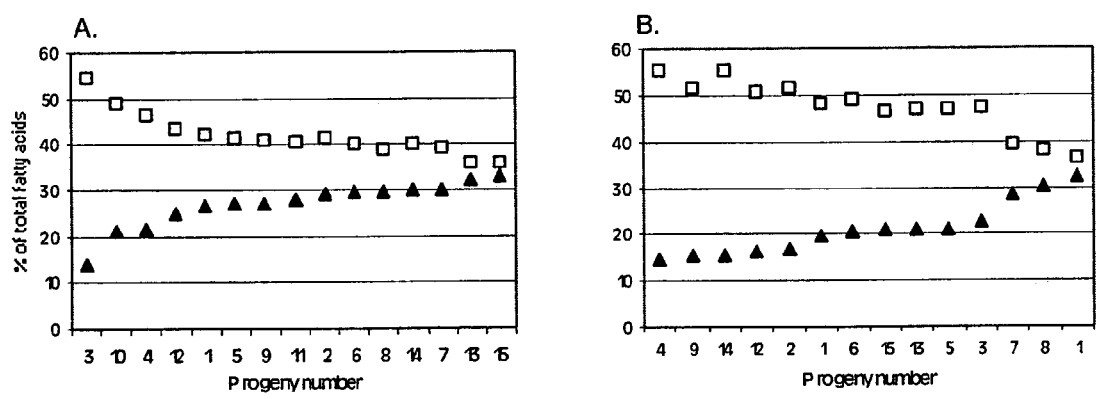
FIG. 9 shows the fatty acid levels in T2 cotton seeds germinated from two of the high-oleate trangenic lines. Oleic acid (triangle) and linoleic acid (open square) levels in T2 seeds from T1 plants of two high oleic acids lines H50-2 (A) and H41-1 (B). A pooled sample of 30 T2 seeds from 15 different T1 plants of each line was tested.

FIG. 9 shows the fatty acid levels in T2 cotton seeds. Seeds were germinated from two of the high-oleate lines and the plants were grown to maturity. Fatty acid analysis was performed on a pooled sample of randomly picked 30 T2 seeds. T2 seeds from Plant #13 and #15 from line H50-2 had oleic acid content of 32.3% and 32.8%, respectively (FIG. 9). Their linoleic acid contents were 35.9% and 36.7%, respectively. In line H41-1, T2 seeds from Plant #1 contained 32% oleic acid and 37% linoleic acid.

As shown in FIG. 9, there was over 80% increase in the levels of oleic acid in the seeds from some of the transgenic lines compared to the wild-type controls. This increase in the oleic acid was associated with a concomitant reduction of approximately 30% in the levels of linoleic acid. As reflected in FIGS. 7–9, the α-globulin promoter effectively manipulates fatty acid levels in oil seeds by driving expression of gene silencing constructs.

Table 2 shows GUS activity in various tissues from control and AGP:gusA transgenic cotton plants that reflects stringent, seed-specific expression of the of α-globulin promoter. Tight regulation of seed-specific promoter expression is important in cases where even a minimal level of promoter activity in the vegetative parts is not acceptable. To determine whether the α-globulin promoter is active exclusively in the seeds and whether the cotton α-globulin promoter can be used to express the transgenes in seeds whose expression in non-seed tissues is undesirable, GUS activity in various tissues from control and AGP:gusA transgenic plants was measured. As shown in Table 2, GUS assays, based on the quantitation of MU (a fluorescent reaction product), show that AGP:gusA gene was expressed only in the seeds and very low levels of fluorescence readings were noted for vegetative and floral tissues.

TABLE 2

GUS activity in various tissues from control and AGP:gusA transgenic cotton plants

| Tissue | GUS activity nmole 4-MU/mg protein/min | |
|---|---|---|
| | Control | AGP:gusA |
| Stem | 0.06 ± 0.008 | 0.018 ± 0.002 |
| Root | 0.139 ± 0.005 | 0.12 ± 0.006 |
| Pollen | 0.018 ± 0.0 | 0.024* |
| Flower bud | 0.801 ± 0.025 | 0.11 ± 0.05 |
| Leaf | 0.037 ± 0.002 | 0.014 ± 0.005 |
| Seed | 0.002 ± 0.0004 | 349.9 ± 55 |

*Number of replicates were not sufficient to calculate SE. Assays were done in triplicates. Numbers are Mean ± Std Error.

Tables 3A and 3B show GUS activity in water-stressed AGP:gusA transgenic plants. Some members of Lea class seed-specific promoters are known to be activated in vegetative tissues by ABA as well as drought conditions (Seffens et al., 1990; Vivekananda et al., 1992, Siddiqui et al., 1998). Exogenous ABA was shown to induce β-phaseolin promoter driving gusA gene in isolated embryos of transgenic tobacco (Bustos et al., 1998). To rule out the possibility that the cotton α-globulin promoter (AGP) may be activated in vegetative parts under water-stress condition that are known to result in increased levels of endogenous ABA, GUS fluorometric assays were performed on leaf extracts of plants from three different transgenic lines that were subjected to water stress by withholding watering. Leaf samples were analyzed for GUS activity at different time points following the last watering until the time they showed complete wilting. As shown in Tables 3A and 3B, no measurable GUS activity was detected in any of the leaf samples from these three transgenic plants even after they were completely wilted. The α-globulin promoter is active exclusively in the seeds and it is not induced in the vegetative parts of the plant by water stress conditions.

TABLE 3A

GUS activity in water stressed AGP:gusA transgenic plants #1 and #2. Assays were performed on leaf extracts.

| | Days after last watering (mnole 4-MU/mg protein/min*) | | | | | | |
|---|---|---|---|---|---|---|---|
| Plant # | 2 days | 3 days | 5 days | 7 days | 8 days | 9 days | 14 days |
| 1 | 0.012 ± 0.0043 | 0.016 ± 0.0046 | 0.0071 ± 0.0027 | 0.014 ± 0.0024 | 0.022 ± 0.0041 | 0.015 ± 0.0034 | 0.01 ± 0.00089 |
| 2 | 0.011 ± 0.0039 | 0.017 ± 0.0057 | 0.0083 ± 0.0036 | 0.01 ± 0.0039 | 0.014 ± 0.0041 | 0.02 ± 0.0034 | 0.001 ± 0.00091 |

TABLE 3B

GUS activity in water stressed AGP:gusA transgenic plant #3. Assays were performed on leaf extracts.

| | Days after last watering (nmole 4-MU/mg protein/min*) | | | | | | |
|---|---|---|---|---|---|---|---|
| Plant # | 2 days | 6 days | 8 days | 10 days | 11 days | 12 days | 17 days |
| 3 | 0.014 ± 0.006 | 0.014 ± 0.0073 | 0.009 ± 0.0022 | 0.012 ± 0.0033 | 0.018 ± 0.0054 | 0.019 ± 0.01 | 0.0013 ± 0.001 |

*Assays were done in triplicates. Numbers are Mean ± Std Error.

It is clear that the 1108 bp α-globulin promoter sequence from cotton can confer a strong seed-specific expression in cottonseed as well as in the seeds of two other dicots. AGP will be useful for any application involving transgene-mediated over-expression or suppression during seed development in dicots, thus adding to the availability of seed-specific promoters.

Various basics of the invention have been explained herein. The various techniques and devices disclosed represent a portion of that which those skilled in the art would readily understand from the teachings of this application. Details for the implementation thereof can be added by those with ordinary skill in the art. The accompanying figures may contain additional information not specifically discussed in the text and such information may be described without adding new subject matter. Additionally, various combinations and permutations of all elements or applications can be created and presented. All can be done to optimize performance in a specific application.

The various steps described herein can be combined with other steps, can occur in a variety of sequences unless otherwise specifically limited, various steps can be interlineated with the stated steps, and the stated steps can be split into multiple steps. Unless the context requires otherwise, the word "comprise" or variations such as "comprises" or "comprising", should be understood to imply the inclusion of a stated element or step or group of elements or steps but not the exclusion of any other element or step or group of elements or steps.

Further, any references mentioned in the application for this patent as well as all references listed in any list of references filed with the application are hereby incorporated by reference. However, to the extent statements might be considered inconsistent with the patenting of this invention such statements are expressly not to be considered as made by the applicant(s).

REFERENCES

An G, Ebert P R, Mitra A and Ha S B (1988) Binary vectors. In: Gelvin S B and Shilperoort R A (eds.) Plant Mol Biol Manual (pp. A3: 1–19) Kluwer Academic Publishers, Dordrecht.

Barker S J, Harada J J and Godberg R B (1988) Cellular localization of soybean storage protein mRNA in transformed tobacco seeds. *Proc Natl Acad Sci* USA 85: 458–462.

Bechtold N and Pelletier G (1998) In planta *Agrobacterium*-mediated transformation of adult *Arabidopsis thaliana* plants by vacuum infiltration. *Methods Mol Biol* 82:259–266.

Bevan M (1984) Binary *Agrobacterium* vectors for plant transformation. Nucleic Acids Res. 12: 8711–8721

Bogue M A, Vonder Haar R A, Nuccio M L, Griffing L R and Thomas T L (1990) Developmentally regulated expression of a sunflower 11S seed protein gene in transgenic tobacco. *Mol Gen Genet* 222: 49–57.

Borroto K and Dure III L (1987) The globulin seed storage proteins of flowering plants are derived from two ancestral genes. *Plant Mol Biol* 8: 113–131.

Bradford M M (1976) A rapid and sensitive method for the quantitation of microgram quantities of protein utilizing the principle of protein-dye binding. *Anal Biochem* 72: 248–254.

Brusslan J A and Tobin E M (1995) Isolation of new promoter-mediated co-suppressed lines in *Arabidopsis thaliana*. *Plant Mol Biol* 27: 809–813.

Bustos M M, Begum D, Kalkan F A, Battraw M J and Hall T C (1991) Positive and negative cis-acting DNA domains are required for spatial and temporal regulation of gene expression by a seed storage protein promoter. *EMBO J* 10: 1469–1479.

Bustos M M, Guiltinan M J, Jordano J, Begum D, Kalkan F A and Hall T C (1989) Regulation of β-glucuronidase expression in transgenic tobacco plants by an A/T-rich, cis-acting sequence found upstream of a French bean β-phaseolin gene. *Plant Cell* 1: 839–853.

Bustos M M, Iyer M and Gagliardi S J (1998) Induction of a β-phaseolin promoter by exogenous abscisic acid in tobacco: developmental regulation and modulation by external sucrose and $Ca^{2+}$ ions. *Plant mol Biol* 37: 265–274.

Cahoon E B, Marillia E-F, Stecca K L, Hall S E, Taylor D C and Kinney A J (2000) Production of fatty acid components of meadowfoam oil in somatic soybean embryos. *Plant Physiol* 124: 243–251.

Chen Z-L, Pan N-S and Beachy R N (1988) A DNA sequence element that confers seed-specific enhancement to a constitutive promoter. *EMBO J* 7: 297–302.

Chlan C A, Borroto K, Kamalay J A and Dure III L (1987) Developmental biochemistry of cottonseed embryogenesis and germination. XIX. Sequences and genomic organization of the α-globulin (vicilin) genes of cottonseed. *Plant Mol Biol* 9: 533–546.

Chuang C-F. and Meyerowitz E. M. (2000) Specific and heritable genetic interference by double-stranded RNA in *Arabidopsis thaliana*. *Proc. Natl. Acad. Sci.* USA 97:4985–4990.

Dahmer M. L., P. D. Fleming, G. B. Collins, and D. F. Hildebrandt. 1989. A rapid screening technique for determining the lipid composition of soybean seeds. *J. Amer. Oil Chem. Soc.* 66: 543–548.

Dickinson C D, Evans R P and Nielsen N C (1988) RY repeats are conserved in the 5'-flanking regions of legume seed-protein genes. *Nucleic Acids Res* 16: 371.

Dure III L (1989) Characteristics of the storage proteins of cotton. *J Am Oil Chem Soc* 66: 356–359.

Dure III L and Chlan C (1981) Developmental biochemistry of cottonseed embryogenesis and germination. XII. Purification and properties of principal storage proteins. *Plant Physiol* 68: 180–186.

Goldberg R B (1986) Regulation of plant gene expression. *Phil Trans R Soc Lond* 314: 343–353.

Goldberg R B, Barker S J, and Perez-Grau L (1989) Regulation of gene expression during plant embryogenesis. *Cell* 56: 149–160.

Goldberg R B, de Paiva G and Yadegari R (1994) Plant embryogenesis: zygote to seed. *Science* 266: 605–614.

Goossens A, Dillen W, De Clercq J, Van Montagu M and Angenon G (1999) The arcelin-5 gene of *Phaseolus vulgaris* directs high seed-specific expression in transgenic *Phaseolus acutifolius* and *Arabidopsis* plants. *Plant Physiol* 120:1095–1104.

Goto F, Yoshihara T, Shigemoto N, Toki S and Takaiwa F (1999) Iron fortification of rice seed by the soybean ferritin gene. *Nat Biotechnology* 17: 282–286.

Higgins T J V (1984) Synthesis and regulation of major proteins in seeds. *Ann Rev Plant Physiol* 35: 191–221.

Hitz W D, Yadav N S, Reiter R S, Mauvais C J and Kinney A J (1995) Reducing polyunsaturation in oils of transgenic canola and soybean. In: Kader J-C and Mazliak (eds.) Plant Lipid Metabolism (pp. 506–508) Kluwer Academic Publishers, Dordrecht.

Horsch R B, Fry J E, Hoffmann N, Neidermeyer J, Rogers S G and Fraley R T (1988) Leaf disc transformation. In: Gelvin S B and Schilperoort R A (eds.) Plant Mol Biol Manual (pp. A5: 1–9) Kulwer Academic Publishers, Dordrecht.

Jefferson R A, Kavanagh T A and Bevan M W (1987) GUS fusions: β-glucuronidase as a sensitive and versatile gene fusion marker in higher plants. *EMBO J* 6: 3901–3907.

Kawagoe Y, Campell B R and Murai N (1994) Synergism between CACGTG (G-box) and CACCTG cis-elements is required for activation of the bean seed storage protein β-phaseolin gene. *Plant J* 5: 885–890.

Kawagoe Y and Murai N (1992) Four distinct nuclear proteins recognize in vitro the proximal promoter of the bean seed storage protein β-phaseolin gene conferring spatial and temporal control. *Plant J* 2: 927–936.

Kim S Y, Chung H-J and Thomas T L (1997) Isolation of a novel class of bZIP transcription factors that interact with ABA-responsive and embryo-specification elements in the Dc3 promoter using a modified yeast one-hybrid system. *Plant J* 11:1237–1251.

Kinney A J (1996) Development of genetically engineered oilseeds: From molecular biology to agronomics. In: Williams J P, Khan M U, Lem N W (eds.), Physiology, Biochemistry and Molecular Biology of Plant Lipids (pp. 298–300) Kluwer, Dordrecht.

H Klee, R Horsch, and S Rogers (1987) *Agrobacterium*-mediated plant transformation and its further applications to plant biology. *Annu. Rev. Plant Physiol. Plant Mol. Biol.* 38: 467–486.

Klein et al. (1987) High-velocity microprojectiles for delivering nucleic acids into living cells. Nature 327: 70.

Lessard P A, Allen R D, Fujiwara T and Beachy R N (1993) Upstream regulatory sequences from two β-conglycinin genes. *Plant Mol Biol* 22: 873–885.

Murashige T and Skoog F (1962) A revised medium for rapid growth and bioassays with tobacco tissue cultures. *Physiol Plant* 15: 473–497.

Napoli et al. (1990) Introduction of a chimeric chalcone synthase gene into petunia results in reversible co-suppression of homologous genes in trans. *The Plant Cell* 2: 270–289.

Nunberg A N, Li Z, Bogue M A, Vivekananda J, Reddy A S and Thomas T L (1994) Developmental and hormonal regulation of sunflower helianthinin genes: Proximal promoter sequences confer regionalized seed expression. *Plant Cell* 6: 473–486.

Nunberg A N, Li Z, Chung H-J, Reddy A S and Thomas T L (1995) Proximal promoter sequences of sunflower helianthinin genes confer regionalized seed-specific expression. *J Plant Physiol* 145: 600–605.

Park Y-D, Papp I, Moscone E A, Iglesias V A, Vaucheret H, Matzke A J M and Matzke M A (1996) Gene silencing mediated by promoter homology occurs at the level of transcription and results in meiotically heritable alterations in methylation and gene activity. *Plant J* 9: 183–194.

Russell D A and Fromm M E (1997) Tissue-specific expression in transgenic maize of four endosperm promoters from maize and rice. Transgenic Res 6: 157–168.

Seffens W S, Almoguera C, Wilde H D, Haar R A V and Thomas T L (1990) Molecular analysis of a phylogenetically conserved carrot gene: developmental and environmental regulation. *Dev Genet* 11: 65–76.

Shintani D and DellaPenna D (1998) Elevating the vitamin E content of plants through metabolic engineering. *Science* 282: 2098–2100.

Siddiqui N U, Chung H-J, Thomas T L and Drew M C (1998) Abscisic acid-dependent and -independent expression of the carrot late-embryogenesis-abundant-class gene Dc3 in transgenic tobacco seedlings. *Plant Physiol* 118: 1181–1190.

Siebert P D, Chenchik A, Kellogg D E, Lukyanov K A and Lukyanov S A (1995) An improved PCR method for walking in uncloned genomic DNA. *Nucleic Acids Res* 23: 1087–1088.

Soltis P S, Soltis D E and Chase M W (1999) Angiosperm phylogeny inferred from multiple genes as a tool for comaparative biology. *Nature* 402: 402–404.

Sun S S M and Larkins B A (1993) Transgenic plants for improving seed storage proteins. In: Kung S-d and Wu R (eds.) Transgenic plants: engineering and utilization Vol. 1 (pp. 339–372) Academic Press, California.

Sunilkumar G., J. P. Connell and A. S. Reddy, C. W. Smith, and K. S. Rathore. (2002) Cotton α-globulin promoter: Isolation and functional characterization in cotton, *Arabidopsis* and tobacco. *Transgenic Research* 11: 347–359.

Sunilkumar G and Rathore K S (2001) Transgenic cotton: factors influencing *Agrobacterium*-mediated transformation and regeneration. *Mol Breeding* 8:37–52.

Van der Krol (1990) Inhibition of flower pigmentation by antisense CHS genes: promoter and minimal sequence requirements for the antisense effect. *Plant Mol. Biol,* 14: 457–466.

Vaucheret H (1993) Identification of a general silencer for 19S and 35S promoters in a transgenic tobacco plant: 90 bp of homology in the promoter sequence are sufficient for trans-inactivation. *C R Acad Sci, Paris* 316: 1471–1483.

Vivekananda J, Drew M C and Thomas T L (1992) Hormonal and environmental regulation of the carrot lea-class gene Dc3. *Plant physiol* 100: 576–581.

Wang M-B. and Waterhouse P. M. (2000) High-efficiency silencing of a β-glucuronidase gene in rice is correlated with repetitive transgene structure but is independent of DNA methylation. *Plant Mol. Biol.* 43: 67–82.

Waterhouse P. M., Graham M. W. and Wang M-B. (1998) Virus resistance and gene silencing in plants can be induced by simultaneous expression of sense and antisense RNA. *Proc. Natl. Acad. Sci.* USA 95:13959–13964.

White P. G. 2000. Fatty acids in oilseeds (vegetable oils). Fatty acids in foods and their health implications. C. K. Chow (ed.) Marcel Dekker, Inc. Pp. 209–238.

Ye X, Al-Babili S, Kloti A, Zhang J, Lucca P, Beyer P and Potrykus I (2000) Engineering the provitamin A (β-carotene) biosynthetic pathway into (carotenoid-free) rice endosperm. *Science* 287: 303–305.

The invention claimed is:

1. A method for obtaining a plant which produces at least one seed having a protein content different from a plant of the same species not obtained by this method, said method comprising:
   (a) transforming a host plant cell with a DNA construct, wherein said construct comprises, as operably linked components, a cotton alpha globulin gene regulatory region comprising a promoter containing a portion of SEQ ID NO: 1 that is capable of promoting seed-specific expression, wherein said portion comprises the cis-elements of SEQ ID NO: 1 which confers seed-specific expression to the promoter, and a DNA sequence encoding a protein, wherein said components are functional in a plant cell, whereby said DNA construct becomes integrated into the genome of said plant cell;
   (b) regenerating a plant from said transformed plant cell;
   (c) obtaining seeds from the regenerated plant of step (b);
   (d) selecting the seeds of step (c) for seed-specific expression of said DNA sequence;
   (e) growing plants from the selected seeds of step (d);
   (f) subjecting plants of step (e) to water stress;
   (g) selecting a plant from the plants of step (f) that does not express said DNA sequence in tissues other than seeds, and wherein said selected plant produces at least one said seed that has said protein content different from a plant of the same species not transformed by said DNA construct.

2. A method for obtaining a plant which produces at least one seed having a protein content different from a plant of the same species not obtained by this method, said method comprising:
   (a) transforming a host plant cell with a DNA construct, wherein said construct comprises, as operably linked components, a cotton alpha globulin gene regulatory region comprising the promoter sequence as set forth in SEQ ID NO: 1 that is capable of promoting seed-specific expression, and a DNA sequence encoding a protein, wherein said components are functional in a plant cell, whereby said DNA construct becomes integrated into the genome of said plant cell;
   (b) regenerating a plant from said transformed plant cell;
   (c) obtaining seeds from the regenerated plant of step (b);
   (d) selecting the seeds of step (c) for seed-specific expression of said DNA sequence;
   (e) growing plants from the selected seeds of step (d);
   (f) subjecting plants of step (e) to water stress;
   (g) selecting a plant from the plants of step (f) that does not express said DNA sequence in tissues other than seeds, and wherein said selected plant produces at least one said seed that has said protein content different from a plant of the same species not transformed by said DNA construct.

3. A method for obtaining a plant which produces at least one seed having a protein content different from a plant of the same species not obtained by this method, said method comprising:
   (a) transforming a host plant cell with a DNA construct, wherein said construct comprises, as operably linked components, a cotton alpha globulin gene regulatory region comprising the promoter sequence as set forth in SEQ ID NO: 2 that is capable of promoting seed-specific expression, and a DNA sequence encoding a protein, wherein said components are functional in a plant cell, whereby said DNA construct becomes integrated into the genome of said plant cell;
   (b) regenerating a plant from said transformed plant cell;
   (c) obtaining seeds from the regenerated plant of step (b);
   (d) selecting the seeds of step (c) for seed-specific expression of said DNA sequence;
   (e) growing plants from the selected seeds of step (d);
   (f) subjecting plants of step (e) to water stress;

(g) selecting a plant from the plants of step (f) that does not express said DNA sequence in tissues other than seeds, and wherein said selected plant produces at least one said seed that has said protein content different from a plant of the same species not transformed by said DNA construct.

4. The method of claim 1, wherein said DNA sequence encoding said protein is heterologous to said promoter.

5. The method of claim 2, wherein expression of said protein alters the fatty acid content of said at least one seed.

6. The method of claim 3, wherein expression of said protein alters the fatty acid content of said at least one seed.

7. A method for obtaining a plant which produces at least one seed having reduced content of an endogenous protein compared to a seed of a non-transformed plant of the same species not obtained by this method, said method comprising:
- (a) transforming a host plant cell with a DNA construct, wherein said construct comprises, as operably linked components, a cotton alpha globulin gene regulatory region comprising the promoter sequence as set forth in SEQ ID NO: 1 that is capable of promoting seed-specific expression, and a DNA sequence that is complementary to a native plant gene encoding said endogenous protein, wherein said components are functional in a plant cell, whereby said DNA construct becomes integrated into the genome of said plant cell;
- (b) regenerating a plant from said transformed plant cell;
- (c) obtaining seeds from the regenerated plant of step (b);
- (d) selecting the seeds of step (c) for seed-specific expression of said DNA sequence;
- (e) growing plants from the selected seeds of step (d);
- (f) subjecting plants of step (e) to water stress;
- (g) selecting a plant from the plants of step (f) that does not express said DNA sequence in tissues other than seeds, and wherein said selected plant produces at least one said seed that has reduced content of said endogenous protein as compared to a seed of a non-transformed plant of the same species.

8. The method of claim 1, wherein said water stress comprises drought.

9. The method of claim 2, wherein said water stress comprises drought.

10. The method of claim 3, wherein said water stress comprises drought.

11. The method of claim 7, wherein said water stress comprises drought.

12. A method for obtaining a plant which produces at least one seed having a reduced content of an endogenous protein compared to a seed of a non-transformed plant of the same species not obtained by this method, said method comprising:
- (a) transforming a host plant cell with a DNA construct, wherein said construct comprises, as operably linked components, a cotton alpha globulin gene regulatory region comprising a promoter containing a portion of SEQ ID NO: 1 that is capable of promoting seed-specific expression, wherein said portion comprises the cis-elements of SEQ ID NO: 1 which confers seed-specific activity to the promoter, and a DNA sequence that is complementary to a native plant gene encoding said endogenous protein, wherein said components are functional in a plant cell, whereby said DNA construct becomes integrated into the genome of said plant cell;
- (b) regenerating a plant from said transformed plant cell;
- (c) obtaining seeds from the regenerated plant of step (b);
- (d) selecting the seeds of step (c) for seed-specific expression of said DNA sequence;
- (e) growing plants from the selected seeds of step (d);
- (f) subjecting plants of step (e) to water stress;
- (g) selecting a plant from the plants of step (f) that does not express said DNA sequence in tissues other than seeds, and wherein said selected plant produces at least one said seed that has reduced content of said endogenous protein as compared to a seed of a non-transformed plant of the same species.

* * * * *

SEQUENCE LISTING

<160> NUMBER OF SEQ ID NOS: 3
<210> SEQ ID NO 1

<211> LENGTH: 1144
<212> TYPE: DNA
<213> ORGANISM: Gossypium hirsutum

<400> SEQUENCE: 1

```
ctattttcat cctatttaga aatccaagtt gacacctaaa atttagttgg actgccatgt      60
aggattatcg ttagagagat aacggagctt aacggtagag tgatcacttt gtaacaaaat     120
aataacaaaa gtgactaaag tgtaacattt caaacataaa tgattaaaat ataacctgag     180
gcaaacaaaa atgactattt ttatagatta ccctaaaatt aaagagtcat ggccctagcc     240
cctcgcctac ttgtttgttt ttaataaact aacatagtat aatatattgt taggattata     300
taaaattatt aataaatagt ataattaatt taaaatttat gaaaaataaa ttaccatatt     360
tcttaaaatac gtggcacctt atgttggatt ggactgtata acttatatac tattatctat     420
attgaatcca aatccttact tttaagcgtt tttagtgaaa cattttattt tccattctta     480
ttatataaat ttatataatg atataatatg taatacttag ataatattat tgaaaaagaa     540
taaaaatacc tcaaactttg aaaggactaa tttgtatgag catcaaacgt acaggatacc     600
aaaagtatac atatctgaat tgttcatat ctcctgcaac tcatagatca tcaccatgca     660
cagcaacatg tgtacacttg acttgtcctc tatcaactca acccttaact cagtgaatcg     720
ggacatctct gtctcacttt aaaacccttc ccagtttcaa cactctttga attcaactga     780
gttcacatac aacacaacac agtccatcat cttttctgctg ttaaagcatc atcatttcgc     840
cccttccagt tacagatgca acatgaaccc ccctgcaaca agtttgtcc gaaccttgct     900
agtaccatgt gaagggatgt ggcatctcga tatctaccca ccactataca aaaaaaaaa     960
aaagagacaa tatttcgtct tctttaattt gcacactcgt catcttgcat gtcaatgtct    1020
tcaacacgtt gatgaagatt tgcatgcaaa atatcaccct tccacagctc caccttctat    1080
aaatacatta ccactctttg ctattaccat cacacagtaa caaaatacag agcttatcgt    1140
aatc                                                                  1144
```

<210> SEQ ID NO 2
<211> LENGTH: 1108
<212> TYPE: DNA
<213> ORGANISM: Gossypium hirsutum

<400> SEQUENCE: 2

```
ctattttcat cctatttaga aatccaagtt gacacctaaa atttagttgg actgccatgt      60
aggattatcg ttagagagat aacggagctt aacggtagag tgatcacttt gtaacaaaat     120
aataacaaaa gtgactaaag tgtaacattt caaacataaa tgattaaaat ataacctgag     180
gcaaacaaaa atgactattt ttatagatta ccctaaaatt aaagagtcat ggccctagcc     240
cctcgcctac ttgtttgttt ttaataaact aacatagtat aatatattgt taggattata     300
taaaattatt aataaatagt ataattaatt taaaatttat gaaaaataaa ttaccatatt     360
tcttaaaatac gtggcacctt atgttggatt ggactgtata acttatatac tattatctat     420
attgaatcca aatccttact tttaagcgtt tttagtgaaa cattttattt tccattctta     480
ttatataaat ttatataatg atataatatg taatacttag ataatattat tgaaaaagaa     540
taaaaatacc tcaaactttg aaaggactaa tttgtatgag catcaaacgt acaggatacc     600
aaaagtatac atatctgaat tgttcatat ctcctgcaac tcatagatca tcaccatgca     660
cagcaacatg tgtacacttg acttgtcctc tatcaactca acccttaact cagtgaatcg     720
ggacatctct gtctcacttt aaaacccttc ccagtttcaa cactctttga attcaactga     780
```

```
-continued gttcacatac aacacaacac agtccatcat ctttctgctg ttaaagcatc atcatttcgc      840
cccttccagt tacagatgca acatgaaccc ccctgcaaca aagtttgtcc gaaccttgct      900
agtaccatgt gaagggatgt ggcatctcga tatctaccca ccactataca aaaaaaaaaa      960
aaagagacaa tatttcgtct tctttaattt gcacactcgt catcttgcat gtcaatgtct     1020
tcaacacgtt gatgaagatt tgcatgcaaa aatatcacct tccacagctc caccttctat     1080
aaatacatta ccactctttg ctattacc                                        1108

<210> SEQ ID NO 3
<211> LENGTH: 336
<212> TYPE: DNA
<213> ORGANISM: Gossypium hirsutum

<400> SEQUENCE: 3
ctattttcat cctatttaga aatccaagtt gacacctaaa atttagttgg actgccatgt       60
aggattatcg ttagagagat aacggagctt aacggtagag tgatcacttt gtaacaaaat      120
aataacaaaa gtgactaaag tgtaacattt caaacataaa tgattaaaat ataacctgag      180
gcaaacaaaa atgactattt ttatagatta ccctaaaatt aaagagtcat ggccctagcc      240
cctcgcctac ttgtttgttt ttaataaact aacatagtat aatatattgt taggattata      300
taaaattatt aataaatagt ataattaatt taaaat                                336
```